(12) United States Patent
Millett

(10) Patent No.: US 10,329,145 B2
(45) Date of Patent: *Jun. 25, 2019

(54) CAPACITIVE INTRAVASCULAR PRESSURE-SENSING DEVICES AND ASSOCIATED SYSTEMS AND METHODS

(71) Applicant: Volcano Corporation, San Diego, CA (US)

(72) Inventor: Bret C. Millett, Folsom, CA (US)

(73) Assignee: VOLCANO CORPORATION, San Diego, CA (US)

( * ) Notice: Subject to any disclaimer, the term of this patent is extended or adjusted under 35 U.S.C. 154(b) by 95 days.

This patent is subject to a terminal disclaimer.

(21) Appl. No.: 15/489,622

(22) Filed: Apr. 17, 2017

(65) Prior Publication Data

US 2017/0283251 A1 Oct. 5, 2017

Related U.S. Application Data

(63) Continuation of application No. 14/133,312, filed on Dec. 18, 2013, now Pat. No. 9,624,095.

(Continued)

(51) Int. Cl.
*G01L 19/00* (2006.01)
*B81C 1/00* (2006.01)
(Continued)

(52) U.S. Cl.
CPC .......... *B81C 1/0023* (2013.01); *A61B 5/0215* (2013.01); *A61B 5/02152* (2013.01);
(Continued)

(58) Field of Classification Search
CPC ..... G01L 19/04; G01L 19/147; G01L 9/0042; G01L 9/0072; G01L 13/025;
(Continued)

(56) References Cited

U.S. PATENT DOCUMENTS 5,207,103 A 5/1993 Wise et al.
9,624,095 B2 * 4/2017 Millett ................. B81C 1/0023
(Continued)

FOREIGN PATENT DOCUMENTS

EP 0230084 7/1987
JP 2003265617 A 9/2003
(Continued)

OTHER PUBLICATIONS

International Searching Authority/European Patent Office, "Communication—Supplementary European Search Report", for European Application No. 13869635.6, dated Oct. 7, 2016, 10 pages.
(Continued)

*Primary Examiner* — Andre J Allen

(57) ABSTRACT

Intravascular devices, systems, and methods are disclosed. In some embodiments, the intravascular devices are guide wires that include a capacitive pressure-sensing component disposed at a distal portion of the guide wire. Methods of making such intravascular devices, including various manufacturing and assembling techniques, are disclosed. Systems associated with such intravascular devices and methods of using such devices and systems are also disclosed.

13 Claims, 17 Drawing Sheets

Related U.S. Application Data

(60) Provisional application No. 61/747,019, filed on Dec. 28, 2012.

(51) Int. Cl.

| | | |
|---|---|---|
| *G01L 19/14* | (2006.01) | |
| *A61B 5/0215* | (2006.01) | |
| *A61B 5/00* | (2006.01) | |
| *A61M 25/00* | (2006.01) | |
| *A61M 25/09* | (2006.01) | |

(52) U.S. Cl.
CPC .......... *A61B 5/6851* (2013.01); *G01L 19/147* (2013.01); *A61B 5/02158* (2013.01); *A61B 2562/0247* (2013.01); *A61B 2562/12* (2013.01); *A61M 2025/0002* (2013.01); *A61M 2025/09175* (2013.01)

(58) Field of Classification Search
CPC ..... G01L 9/0054; G01L 9/0075; G01L 19/14; G01L 19/0069; G01L 19/0084; G01L 19/0645; G01L 9/0052; G01L 19/0038; G01L 19/0092; G01L 19/0618; G01L 11/025; G01L 19/0046; G01L 19/06; G01L 19/0681; G01L 19/143; G01L 7/00; G01L 9/00; G01L 9/0041; G01L 9/0044; G01L 9/0051; G01L 9/0055; G01L 9/0073; G01L 19/0007; G01L 19/0023; G01L 19/0627; G01L 19/0672; G01L 19/142; G01L 19/16; G01L 27/002; G01L 7/08; G01L 7/163; G01L 7/166; G01L 9/0047; G01L 11/02; G01L 11/04; G01L 15/00; G01L 19/0609; G01L 19/069; G01L 19/083; G01L 19/148; G01L 1/18; G01L 1/26; G01L 9/0048; G01L 9/006; G01L 9/007; G01L 9/0076; G01L 9/06; G01L 9/065; G01L 9/12; G01L 9/125; G01L 11/00; G01L 13/00; G01L 17/00; G01L 19/00; G01L 19/0015; G01L 19/003; G01L 19/0076; G01L 19/02; G01L 19/08; G01L 19/10; G01L 19/141; G01L 19/145; G01L 1/142; G01L 1/2262; G01L 1/2287; G01L 1/246; G01L 21/12; G01L 23/16; G01L 27/005; G01L 27/007; G01L 7/04; G01L 7/063; G01L 7/082; G01L 7/084; G01L 7/16; G01L 9/0002; G01L 9/0007; G01L 9/0016; G01L 9/0019; G01L 9/0022; G01L 9/0027; G01L 9/0033; G01L 9/0039; G01L 9/0045; G01L 9/005; G01L 9/0058; G01L 9/0077; G01L 9/0079; G01L 9/008; G01L 9/0092; G01L 9/0095; G01L 9/025; G01L 9/04; G01L 9/045; G01L 9/08; G01L 9/085; G01L 9/105; G01L 9/14; G01L 9/16
USPC .................................................. 73/700–756
See application file for complete search history.

(56) References Cited

U.S. PATENT DOCUMENTS

| | | |
|---|---|---|
| 2003/0097064 A1 | 5/2003 | Talpade et al. |
| 2005/0251031 A1 | 11/2005 | Smith |
| 2005/0268724 A1 | 12/2005 | Tenerz |
| 2010/0113967 A1 | 5/2010 | Bobo, Sr. |
| 2012/0041295 A1 | 2/2012 | Schultz |
| 2014/0005560 A1 | 1/2014 | Burkett |
| 2014/0005561 A1 | 1/2014 | Burkett |
| 2014/0187982 A1 | 7/2014 | Millett et al. |
| 2014/0276117 A1 | 9/2014 | Burkett |
| 2015/0032066 A1 | 1/2015 | Burkett |
| 2015/0141853 A1 | 5/2015 | Miller, III et al. |
| 2015/0173629 A1 | 6/2015 | Corl et al. |
| 2015/0297138 A1 | 10/2015 | Burkett et al. |
| 2018/0184981 A1* | 7/2018 | Richardson .......... A61B 5/6851 |

FOREIGN PATENT DOCUMENTS

| | | |
|---|---|---|
| JP | 2007256287 A | 10/2007 |
| WO | 9626670 | 9/1996 |

OTHER PUBLICATIONS

International Searching Authority/European Patent Office, "Supplementary Partial European Search Report", for European Application No. 13869635.6, dated Jun. 29, 2016, 7 pages.

International Search Report and Written Opinion received in Patent Cooperation Treaty Application No. PCT/US2013/076352, dated Apr. 15, 2014, 9 pages.

* cited by examiner

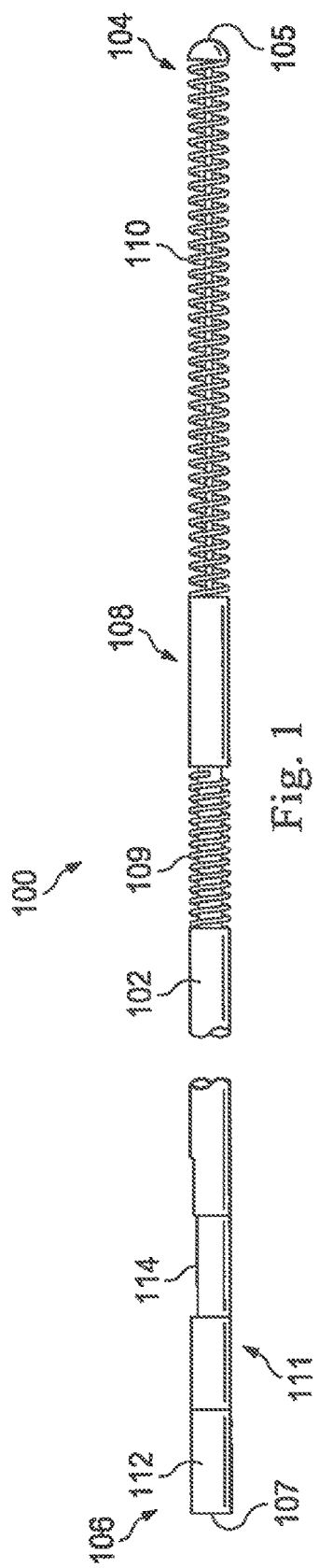
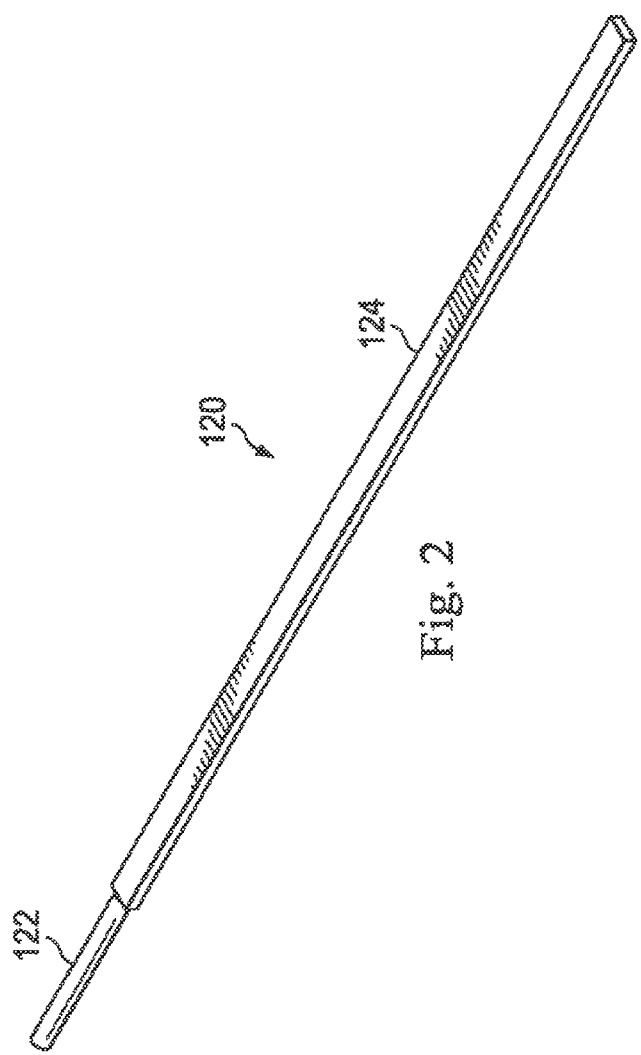

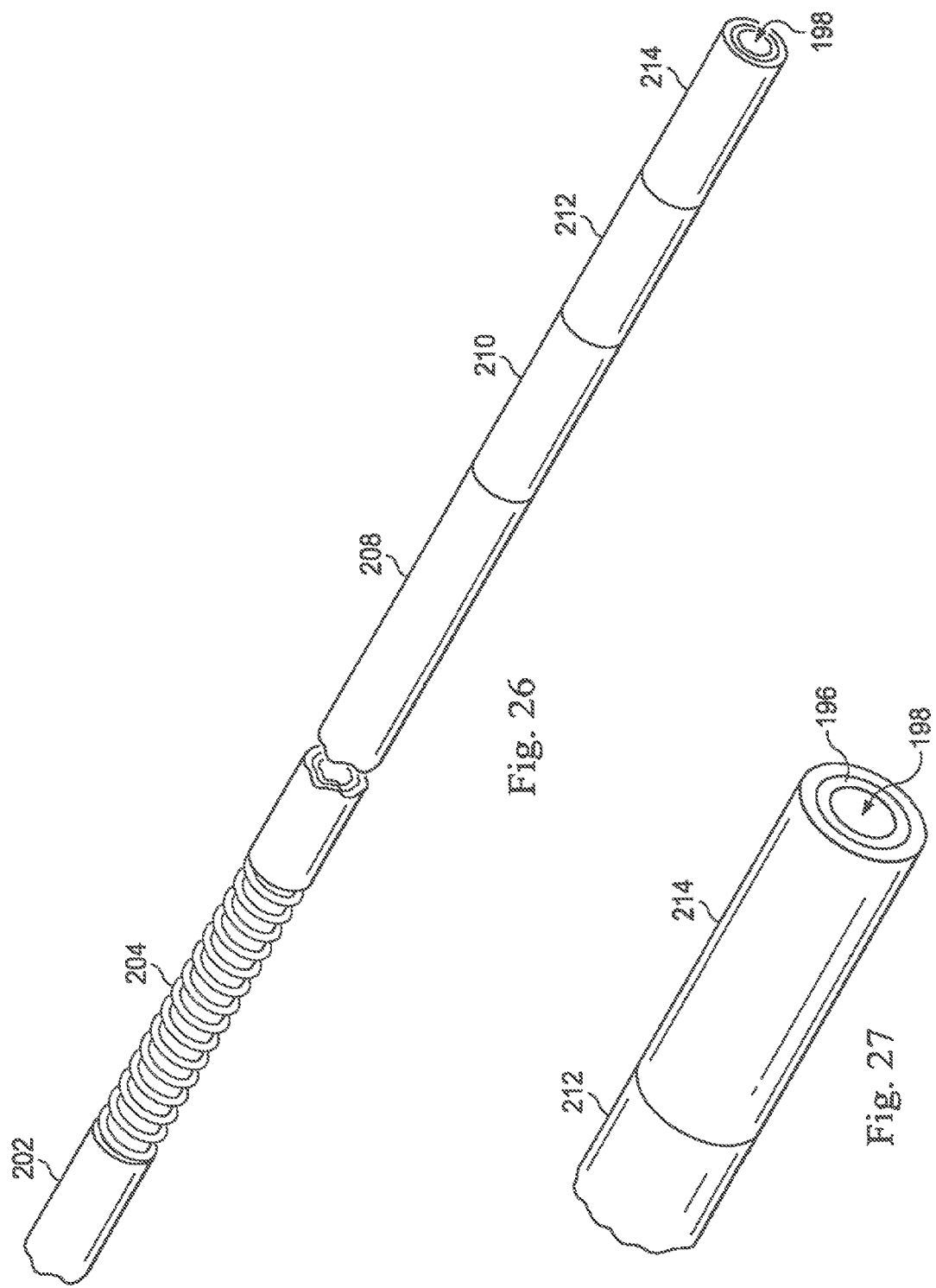

CAPACITIVE INTRAVASCULAR PRESSURE-SENSING DEVICES AND ASSOCIATED SYSTEMS AND METHODS

CROSS-REFERENCE TO RELATED APPLICATIONS

This is a continuation of U.S. patent application Ser. No. 14/133,312, which was filed Dec. 18, 2013, which claims priority to U.S. Patent Application No. 61/747,019, filed Dec. 28, 2012, and the entirety of each of which is incorporated herein by reference.

TECHNICAL FIELD

The present disclosure relates to intravascular devices, systems, and methods. In some embodiments, the intravascular devices are guide wires that include a capacitive pressure-sensing component.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. For example, the handling performance of previous guide wires containing electronic components have been hampered, in some instances, by the need to physically couple the proximal end of the device to a communication line in order to obtain data from the guide wire, the limited space available for the core wire after accounting for the space needed for the conductors or communication lines of the electronic component(s), the stiffness and size of the rigid housing containing the electronic component(s), and/or other limitations associated with providing the functionality of the electronic components in the limited space available within a guide wire.

Accordingly, there remains a need for improved intravascular devices, systems, and methods that include pressure-sensing components.

SUMMARY

Embodiments of the present disclosure are directed to intravascular devices, systems, and methods.

In one embodiment, a guide wire is provided. The guide wire comprises a first elongate flexible element having a proximal portion and a distal portion, the first elongate flexible element being formed of a conductive material; a second elongate flexible element positioned around the first elongate flexible element, the second elongate flexible element being formed of a conductive material and having an outer diameter of 0.018", 0.014", or less; a radial capacitive pressure sensing structure coupled to the distal portion of the first elongate flexible element, the radial capacitive pressure sensing structure having a flexible membrane positioned around at least a portion of a cavity and a conductive member positioned around at least a portion of the flexible membrane such that the conductive member is displaced by changes in ambient pressure relative to a pressure in the cavity; and an application-specific integrated circuit (ASIC) coupled to the distal portion of the elongate flexible element, the ASIC in electrical communication with the conductive member of the radial capacitive pressure sensing component and the first and second flexible elongate elements.

In some instances, a section of the proximal portion of the first elongate flexible element is electrically coupled to a first conductive band. Further, in some instances a section of a proximal portion of the second elongate flexible element defines a second conductive band, such that the first conductive band is positioned proximal of the second conductive band. In some embodiments, the guide wire further includes an insulating member positioned between the first and second conductive bands, the insulating member being positioned around the first elongate flexible element. In some implementations, a majority of the second elongate flexible element is electrically isolated from the first elongate flexible element by a non-conductive layer covering the first elongate flexible element. The cavity of the radial capacitive pressure sensing structure includes a lumen of housing in some instances. In some embodiments, the housing includes a plurality of openings in a sidewall of the housing that are in communication with the lumen. In some instances, the plurality of openings are formed radially around a circumference of the housing where the housing has a cylindrical profile.

In another embodiment, an intravascular pressure-sensing system is provided. The system comprises a pressure-sensing guide wire having features similar to those described above; a processing system configured to process the data obtained by the pressure-sensing guide wire; and an interface configured to communicatively couple the pressure-sensing guide wire to the processing system.

In another embodiment, method of making a pressure-sensing apparatus is provided. The method includes: providing a first conductive tubular member, the first conductive tubular member having a lumen extending along its length; forming a plurality of openings through a sidewall of the first conductive tubular member, the plurality of openings in communication with the lumen of the first conductive tubular member; filling a portion of the lumen of the first conductive tubular member and the plurality of openings with a temporary material; forming a band of the temporary material around an outer surface of the first conductive tubular member, the band of the temporary material formed over the plurality of openings; forming a layer of flexible material over the first conductive tubular member such that the layer of flexible material covers the band of the temporary material; removing the temporary material filling the portion of the lumen and the plurality of openings; and removing the band of temporary material such that a space is created between an inner surface of the layer of flexible material and the outer surface of the first conductive member adjacent each of the plurality of openings such that the layer of flexible material is responsive to changes in ambient pressure relative to a pressure in the lumen of the first conductive tubular member.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 1 is a diagrammatic, schematic side view of an intravascular device according to an embodiment of the present disclosure.

Collectively, FIGS. 2-27 illustrate various aspects of manufacturing and/or assembling the intravascular device of FIG. 1 according to embodiments of the present disclosure.

FIG. 2 is a diagrammatic perspective view of a distal core portion of the intravascular device according to an embodiment of the present disclosure.

FIG. 3 is a diagrammatic perspective view of an expander coupled to the distal core portion of FIG. 2 according to an embodiment of the present disclosure.

FIG. 4 is a diagrammatic perspective view of a tubular member coupled to the expander of FIG. 3 according to an embodiment of the present disclosure.

FIG. 5 is a diagrammatic perspective view of the tubular member coupled to the expander, similar to that of FIG. 4, but showing removal of portions of the tubular member and/or expander according to an embodiment of the present disclosure.

FIG. 6 is a diagrammatic perspective view of the tubular member coupled to the expander, similar to that of FIGS. 4 and 5, but showing the tubular member and expander in phantom with a temporary structure filling open space within the tubular member according to an embodiment of the present disclosure.

FIG. 7 is a diagrammatic perspective view of the tubular member coupled to the expander similar to that of FIG. 6, but with a temporary annular band formed around a portion of the tubular member according to an embodiment of the present disclosure.

FIG. 8 is a diagrammatic perspective view of the tubular member, expander, and distal core portion coated with a material layer according to an embodiment of the present disclosure.

FIG. 9 is a diagrammatic perspective view of the tubular member coupled to the expander after formation of the material layer of FIG. 8, where a section of the material layer surrounding the tubular member is shown in phantom to allow the temporary structure and temporary annular band to be visualized according to an embodiment of the present disclosure.

FIG. 10 is a diagrammatic perspective, side view of the tubular member coupled to the expander after removal of the temporary structure and the temporary annular band according to an embodiment of the present disclosure.

FIG. 11 is a diagrammatic perspective, cross-sectional side view of the tubular member coupled to the expander after removal of the temporary structure and the temporary annular band according to an embodiment of the present disclosure.

FIG. 12 is a close up of a portion of the diagrammatic perspective, cross-sectional side view of the tubular member coupled to the expander of FIG. 11.

FIG. 13 is a diagrammatic, schematic cross-sectional side view of a section of the tubular member and a section of the material layer after removal of the temporary structure and the temporary annular band according to an embodiment of the present disclosure.

FIG. 14 is a diagrammatic perspective view of the tubular member coupled to the expander with an electrode formed on a portion of the material layer surrounding the tubular member according to an embodiment of the present disclosure.

FIG. 15 is a diagrammatic perspective view of the tubular member coupled to the expander, but showing removal of a section of the material layer and coupling of a flexible elongate member to the tubular member according to an embodiment of the present disclosure.

FIG. 16 is a diagrammatic perspective view of the tubular member coupled to the flexible elongate member of FIG. 15, but showing application of a dielectric to a portion of the tubular member according to an embodiment of the present disclosure.

FIG. 17 is a diagrammatic perspective view of the tubular member coupled to the flexible elongate member similar to that of FIG. 16, but showing another electrode formed on a portion of the material layer surrounding the tubular member according to an embodiment of the present disclosure FIG. 18 is a diagrammatic perspective view a portion of the tubular member showing a plurality of conductive pads formed thereon according to an embodiment of the present disclosure.

FIG. 19 is a diagrammatic perspective view a portion of the tubular member showing an application-specific integrated circuit (ASIC) mounted to the plurality of conductive pads of FIG. 18 according to an embodiment of the present disclosure.

FIG. 20 is a diagrammatic perspective view of the flexible elongate member and the tubular member showing formation of a conductive layer over an insulating layer surrounding a majority of the flexible elongate member according to an embodiment of the present disclosure.

FIG. 21 is a diagrammatic perspective view of a distal portion of the flexible elongate member and the tubular member showing a conductive spacer being positioned around the distal portion of the flexible elongate member adjacent to the tubular member according to an embodiment of the present disclosure.

FIG. 22 is a diagrammatic perspective view of the flexible elongate member and the tubular member showing a flexible element being positioned around the distal portion of the flexible elongate member adjacent to the conductive spacer of FIG. 21 and the tubular member and the conductive spacer coated with an insulating material layer according to an embodiment of the present disclosure.

FIG. 23 is a diagrammatic perspective view of the flexible elongate member and the tubular member showing a conductive tubular member positioned around a majority of the flexible elongate member and adjacent the flexible element of FIG. 22 according to an embodiment of the present disclosure.

FIG. 24 is a diagrammatic perspective view of the flexible elongate member and the conductive tubular member of FIG. 23 with an insulating material layer formed around a portion of the conductive tubular member according to an embodiment of the present disclosure.

FIG. 25 is a diagrammatic perspective view of the flexible elongate member and the conductive tubular member similar to that of FIG. 24, but showing an insulating spacer positioned around the flexible elongate member proximal of a proximal end of the conductive tubular member according to an embodiment of the present disclosure.

FIG. 26 is a diagrammatic perspective view of the flexible elongate member and the conductive tubular member similar to that of FIG. 25, but showing a conductive sleeve positioned around the flexible elongate member proximal of a proximal end of the insulating spacer according to an embodiment of the present disclosure.

FIG. 27 is a diagrammatic perspective end view of the conductive sleeve positioned around the flexible elongate member according to an embodiment of the present disclosure.

DETAILED DESCRIPTION

Figure 3:
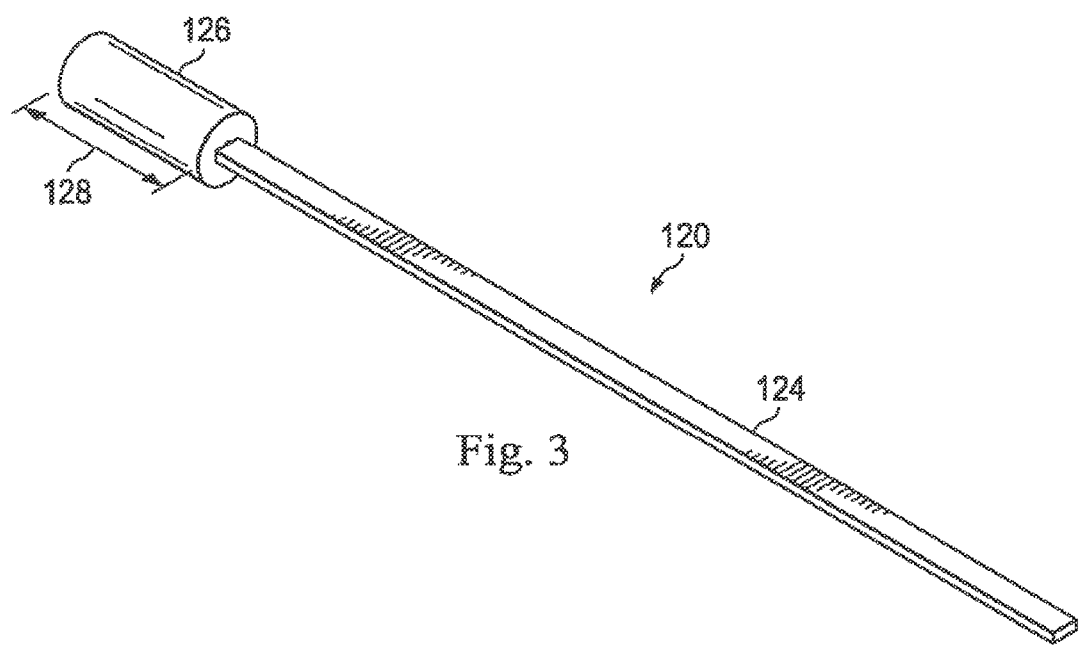

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected", "coupled", and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102, a distal portion 104 adjacent a distal end 105, and a proximal portion 106 adjacent a proximal end 107. A component 108 is defined within the distal portion 104 of the flexible elongate member 102 proximal of the distal tip 105. Generally, the component 108 is representative of one or more electronic, optical, or electro-optical components. In that regard, the component 108 may be a pressure sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. As described below, in some particular embodiments of the present disclosure, the component 108 is a capacitive pressure sensor and associated components. In some instances, the component 108 is positioned less than 10 cm, less than 5, or less than 3 cm from the distal tip 105.

In the illustrated embodiment, the component 108 is positioned between a proximal flexible element 109 and a distal flexible element 110. The proximal flexible elements 109, 110 typically have an increased flexibility relative to the flexible elongate member 102. To that end, in some embodiments one or both of the flexible elements is a coil, a polymer tubing, a polymer tubing embedded with a coil, and/or combinations thereof. In that regard, the coils may take on any suitable form including round wire, flat wire, round and flat wire, constant gauge wire, variable gauge wire, constant pitch, variable pitch, single coil, multiple coils, overlapping coils, threading coils, and/or combinations thereof. In some instances, the component 108 is positioned within a housing. In that regard, the housing is a separate component secured to the proximal and distal flexible element 109, 110 in some instances. In other instances, the housing is integrally formed as a part of at least one of the flexible elements 109, 110. To that end, in some instances the proximal and distal flexible element 109, 110 are formed of a single, continuous flexible element with the component 108 secured thereto.

The intravascular device 100 also includes a connector 111 adjacent the proximal portion 106 of the device. In the illustrated embodiment, the proximal-most portion of the connector 111 is extends to the proximal end 107 of the intravascular device 100. In other instances, the proximal-most portion of the connector 111 is spaced from the proximal end 107 of the flexible elongate member 102. Generally, the spacing of the connector from the proximal end 107 is between 0% and 50% of the total length of the intravascular device 100. While the total length of the intravascular device can be any length, in some embodiments the total length is between about 1300 mm and about 4000 mm, with some specific embodiments have a length of 1400 mm, 1900 mm, and 3000 mm. Accordingly, in some instances the connector 111 is spaced from the proximal end 107 between about 0 mm and about 1400 mm. In some specific embodiments, the connector 111 is spaced from the proximal end by a distance of 0 mm, 300 mm, and 1400 mm.

The connector 111 is configured to facilitate communication between the intravascular device 100 and another device. More specifically, in some embodiments the connector 111 is configured to facilitate communication of data obtained by the component 108 to another device, such as a computing device or processor. Accordingly, in some embodiments the connector 111 is an electrical connector. In such instances, the connector 111 provides an electrical connection to one or more electrical conductors that extend along the length of the flexible elongate member 102 and are electrically coupled to the component 108. In other embodiments, the connector 111 is an optical connector. In such instances, the connector 111 provides an optical connection to one or more optical communication pathways (e.g., fiber optic cable) that extend along the length of the flexible elongate member 102 and are optically coupled to the component 108. Further, in some embodiments the connector 111 provides both electrical and optical connections to both electrical conductor(s) and optical communication pathway(s) coupled to the component 108. In that regard, it should again be noted that component 108 is comprised of a plurality of elements in some instances. In some instances, the connector 111 is configured to provide a physical connection to another device, either directly or indirectly. In other instances, the connector 111 is configured to facilitate wireless communication between the intravascular device 100 and another device. Generally, any current or future developed wireless protocol(s) may be utilized. In yet other instances, the connector 111 facilitates both physical and wireless connection to another device.

As noted above, in some instances the connector 111 provides a connection between the component 108 of the intravascular device 100 and an external device. Accordingly, in some embodiments one or more electrical conductors, one or more optical pathways, and/or combinations thereof extend along the length of the flexible elongate member 102 between the connector 111 and the component 108 to facilitate communication between the connector 111 and the component 108. Generally, any number of electrical conductors, optical pathways, and/or combinations thereof can extend along the length of the flexible elongate member 102 between the connector 111 and the component 108. In some instances, between one and ten electrical conductors and/or optical pathways extend along the length of the flexible elongate member 102 between the connector 111 and the component 108. For the sake of clarity and simplicity, the embodiments of the present disclosure described below and shown in FIG. 1, include two electrically conductive bands 112, 114 that are each coupled to an electrically conductive element extending the length of the flexible elongate member 102 to component 108. In that regard, two electrically conductive bands 112, 114 and associated conductive elements is particularly suited for use with the capacitive pressure sensing system of the present disclosure. However, it is understood that the total number of communication pathways and/or the number of electrical conductors and/or optical pathways is different in other embodiments. More specifically, the number of communication pathways and the number of electrical conductors and optical pathways extending along the length of the flexible elongate member 102 is determined by the desired functionality of the component 108 and the corresponding elements that define component 108 to provide such functionality.

Referring now to FIGS. 2-27, shown therein are various steps and/or aspects of manufacturing and/or assembling the intravascular device of FIG. 1 according to embodiments of the present disclosure. In that regard, the FIGS. 2-27 will be described in the context of steps associated with manufacturing and/or assembling the intravascular device. It is understood that the described steps are exemplary in nature and that one or more of the steps may be omitted, one or more additional steps may be added, and/or the order of the steps may be changed without departing from the scope of the present disclosure. Further, one skilled in the art will recognize that there are alternative ways or manners of achieving the same results as the steps described below and that such alternative techniques are included within the scope of the present disclosure.

Referring initially to FIG. 2, shown therein is a distal core 120 of the intravascular device according to an embodiment of the present disclosure. As shown, the distal core 120 includes a proximal portion 122 having a generally cylindrical profile and a distal portion 124 having a generally rectangular profile. In some instances, the distal portion 124 is formed by flattening a portion of the distal core 120 that initially has a cylindrical profile. Generally, the distal portion 124 is configured to extend to a distal tip or end of the intravascular device. In some instances, a flexible element is positioned around the distal portion 124 of the distal core 120, such as flexible element 110 described with respect to FIG. 1. The distal core 120 may be formed of any suitable material, including without limitation stainless-steel, nitinol, optical fiber, and/or other suitable material or combination of materials. In the illustrated embodiment, the distal core 120 is formed of stainless-steel.

Referring now to FIG. 3, an expander 126 is shown positioned around the proximal portion 122 of the distal core 120. In particular, the expander 126 is positioned around the proximal portion 122 of the distal core 120 such that distal ends of the expander 126 and the proximal portion 122 are aligned along the length of the distal core 120. However, such alignment is not required and, in other embodiments, the distal ends are offset along the longitudinal axis of the distal core 120. The expander has a generally cylindrical profile and, serves to expand the radial diameter of the proximal portion 122 of the distal core 120. To that end, in some instances the proximal portion 122 has a diameter between about 0.05 mm and about 0.15 mm, while the expander 126 has an inner-diameter slightly larger than proximal portion 122 and an outer-diameter between about 0.15 mm and about 0.35 mm. Further, the expander 126 has an axial length 128. In some implementations, the axial length 128 of the expander 126 is between about 0.5 mm and about 6.0 mm. In some instances, the axial length 128 of the expander 126 is equal to the axial length of the proximal portion 122. In other instances, the axial length 128 of the expander 126 is shorter or longer than the axial length of the proximal portion 122. In some instances, the inner-diameter of the expander 126 extends the entire axial length 128, while in other instances, the inner-diameter of the expander 126 does not extend the entire axial length 128. The expander 126 may be formed of any suitable material, including without limitation stainless-steel, nitinol, optical fiber, and/or other suitable material or combination of materials. In some implementations, the expander 126 is formed, at least partially, of conductive material. The expander 126 is fixedly secured and sealed against pressure loss to the proximal portion 122 of the distal core 120 utilizing suitable techniques for the selected materials of the expander 126 and the proximal portion 122 of the distal core 120. Accordingly, in some instances the expander 126 is fixedly secured to the proximal portion 122 of the distal core 120 by solder, weld, adhesive, swaging, and/or combinations thereof In the illustrated embodiment, the expander 126 is formed of stainless-steel and is laser welded to the proximal portion 122 of the distal core 120.

Figure 4:
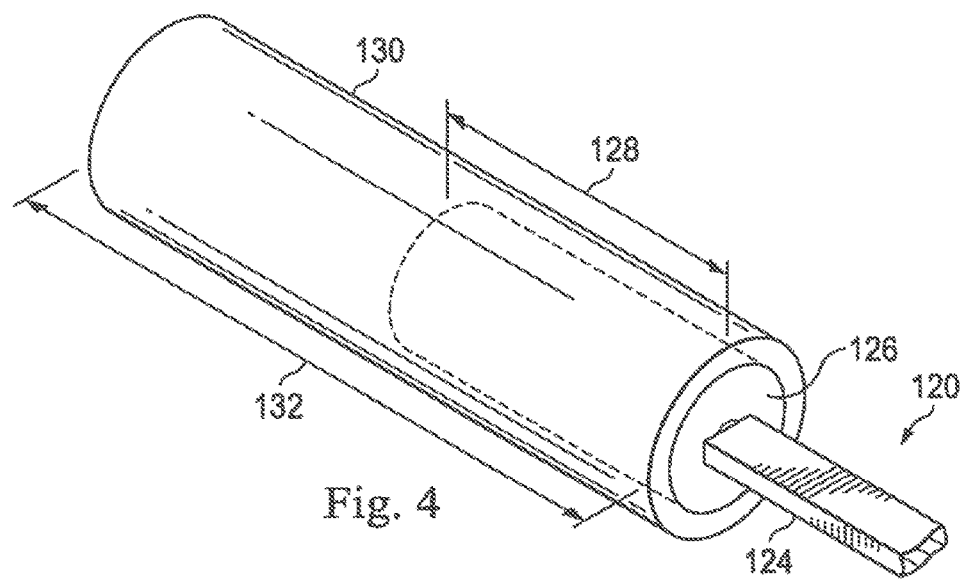

Referring now to FIG. 4, a tubular member 130 is shown positioned around the expander 126. In that regard, the expander has a generally cylindrical profile and, therefore, further expands the radial diameter of the expander. To that end, in some instances the tubular member 130 has an inner-diameter slightly larger than the outer-diameter of expander 126 and an outer-diameter between about 0.15 mm and about 0.35 mm. In the illustrated embodiment, the tubular member 130 is positioned around the expander 126 such that distal ends of the tubular member 130 and the expander 126 are aligned along the length of the proximal portion 122. However, such alignment is not required and, in other embodiments, the distal ends are offset along the longitudinal axis of the proximal portion 122. Further, the tubular member 130 has an axial length 132 that may be greater than, equal to, or less than the axial length 128 of the expander 126. In the illustrated embodiment, the axial length 132 of the tubular member 130 is greater than the axial length 128 of the expander 126. In some implementations, the axial length 132 of the tubular member 130 is between about 0.5 mm and about 6.0 mm. As will be discussed in greater detail below, the increased length or axial offset of the tubular member 130 relative to the expander 126 allows a central lumen of the tubular member 130 to be only partially occupied by the expander 126 (and proximal portion 122 of the distal core 120). In the illustrated embodiment, with the distal ends of the tubular member 130 and the expander 126 aligned and a tubular member 130 with an axial length 132 greater than the axial length 128 of expander 126, a cavity is created in the central lumen equal to the difference between the axial length 132 and the axial length 128. This open space in the lumen of the tubular member 130 is utilized to facilitate capacitive pressure measurements in some implementations of the present disclosure.

The tubular member 130 may be formed of any suitable material, including without limitation stainless-steel, nitinol, optical fiber, polymer, copper, gold, and/or other suitable material or combination of materials. In some implementations, the tubular member 130 is formed, at least partially, of conductive material. For example, in some instances the tubular member is formed first of a non-conductive material, then coated with a conductive material. In such instances, all or only portions of the tubular member may be coated with the conductive material. The tubular member 130 is fixedly secured to the expander 126 utilizing suitable techniques for the selected materials of the tubular member 130 and the expander 126. Accordingly, in some instances the tubular member 130 is fixedly secured to the expander 126 by solder, weld, adhesive, pressed, swaged, and/or combinations thereof. In the illustrated embodiment, the tubular member 130 is formed of stainless-steel and is laser welded to the extender 126. Thus, in the illustrated embodiment the tubular member 130 is electrically coupled to the extender 126. In other embodiments, the tubular member 130 and the extender 126 are micro-molded as one device then welded, glued, soldered, pressed, swaged, and/or otherwise coupled to proximal portion 122 of the distal core 120. Similarly, in some implementations a shape corresponding to the shape resulting from the tubular member 130 and the extender 126 is over-molded directly onto the proximal portion 122 of the distal core 120. The over-molded materials can be conductive or non-conductive. If a non-conductive material is utilized, then a conductive coating could be applied as described above. Generally speaking, the assembly consisting of the distal core 120, the expander 126, and the tubular member 130 may be thought of as the substrate of an electrical device (like a printed-circuit board or flex-circuit) or an "anode" or static member of a capacitive sensor.

Figure 5:
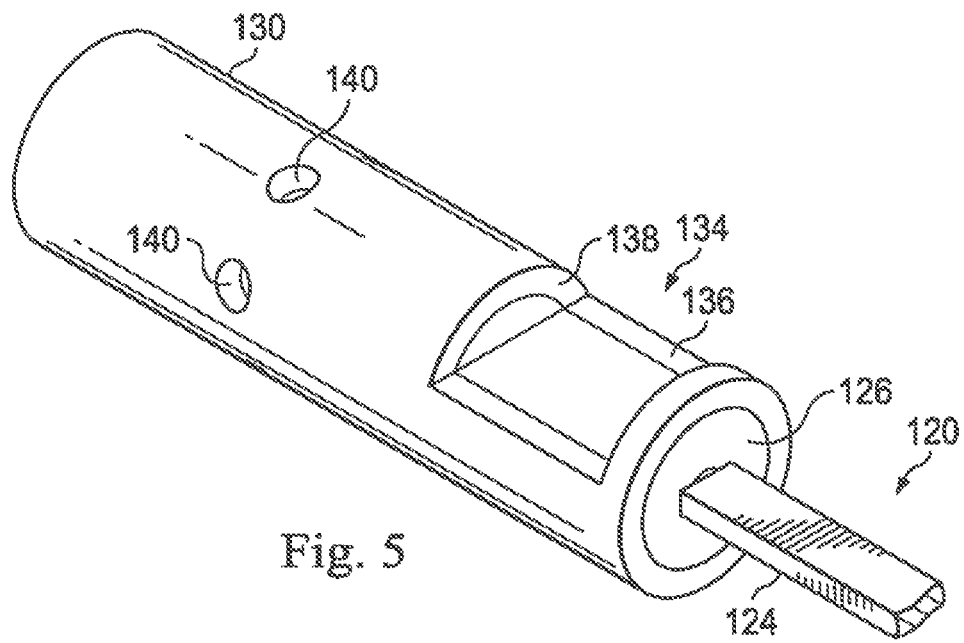

Referring now to FIG. 5, portions of the tubular member 130 and the expander 126 have been removed according to an embodiment of the present disclosure. In particular, a mounting structure 134 has been defined by removal of portions of the tubular member 130 and the expander 126. The mounting structure 134 is sized and shaped to facilitate mounting and interconnection of one or more electrical, optical, and/or electro-optical components. Accordingly, the mounting structure 134 can take on virtually any shape desirable for mounting such components. In the illustrated embodiment, the mounting structure 134 has a generally rectangular profile with a planar bottom surface 136 bounded by a proximal wall 138 and distal wall opposite the proximal wall. As will be described below, the mounting structure 134 of the illustrated embodiment is sized and shaped to facilitate the mounting of an application-specific integrated circuit (ASIC), including electrical coupling of the ASIC to associated components of the intravascular device. Further, a plurality of openings 140 are formed in the tubular member 130 to provide access to the central lumen of the tubular member. Generally, any number of openings may be utilized, but in some instances between 1 and 20 openings are formed. In the illustrated embodiment, the openings 140 are formed annularly around the circumference of the tubular member 130. In that regard, the openings may be equally spaced about the circumference, symmetrically spaced about the circumference, or irregularly spaced about the circumference. Further, in the illustrated embodiment the openings 140 have circular cross-sectional profiles. However, it is understood that the openings may have virtually any geometric (e.g., triangle, rectangle, square, circle, oval, ellipse, trapezoid, pentagon, hexagon, etc.) or non-geometric cross-sectional profile.

Generally, the portions of the tubular member 130 and the expander 126 may be removed using any suitable technique for the applicable material. For example, in some instances the portions of the tubular member 130 and the expander 126 are removed using laser, EDM, micro-drill, grinding, CNC, other suitable techniques, and/or combinations thereof. Further, it is understood that in some instances that portions of the tubular member 130 and/or the expander 126 are removed prior to assembly of the tubular member 130 onto the expander 126 and/or prior to assembly of the expander 126 onto the proximal portion 122 of the distal core 120. Further still, in some instances a plurality of tubular members 130 are formed from a single elongated hypotube. In that regard, the single elongated hypotube may be cut into a plurality of sections, each having the axial length 132. Also, the portions of tubular member 130 shown as being removed in FIG. 5 may likewise be removed while in the form of the single elongated hypotube (e.g., by repeatedly removing the requisite portions along the length of the elongated hypotube at spacings necessary to form the plurality of tubular members) or after formation of the individual tubular member components. Likewise, a plurality of expanders 126 are formed from a single elongated hypotube in some instances. In that regard, the single elongated hypotube may be cut into a plurality of sections, each having the axial length 128. Also, the portions of expander 126 shown as being removed in FIG. 5 in the context of mounting structure 134 may likewise be removed while in the form of the single elongated hypotube (e.g., by repeatedly removing the requisite portions along the length of the elongated hypotube at spacings necessary to form the plurality of expanders) or after formation of the individual expander components.

Figure 6:
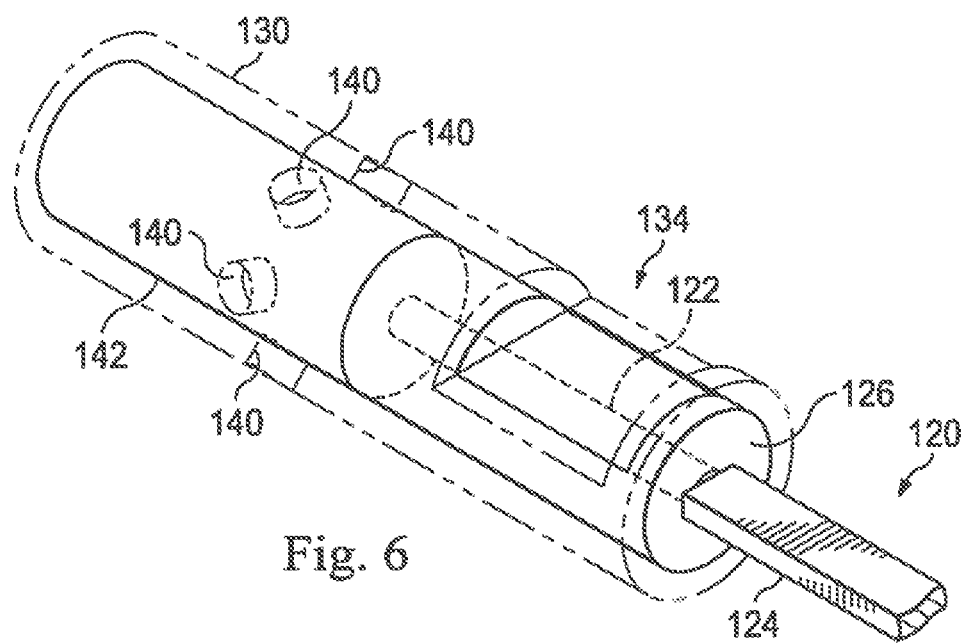

Referring now to FIG. 6, a material 142 has been introduced into the lumen of the tubular member 130 to fill the open space within the tubular member 130, including the central lumen and openings 140. The material 142 forms a temporary structure that will be removed subsequently. Accordingly, the material 142 is formed of a material that can be chemically removed without damaging the tubular member 130, expander 126, and/or the proximal portion 122 of the distal core 120 in some instances. For example, in some instances the material 142 could be copper (Cu).

In some instances, the surface of tubular member 130 is precision center-ground and polished. Further, in some instances a precision groove is optionally cut or ground into the tubular member 130. In that regard, the groove is sized and shaped to receive an annular band 144 described in greater detail below. Accordingly, in some instances the groove is formed prior to the introduction of material 142 such that the material 142 fills the groove. In some instances, the groove filled with the material 142 is precision center-ground and polished to be smooth such that it has the same outer diameter as the remaining portions of tubular member 130.

Figure 7:
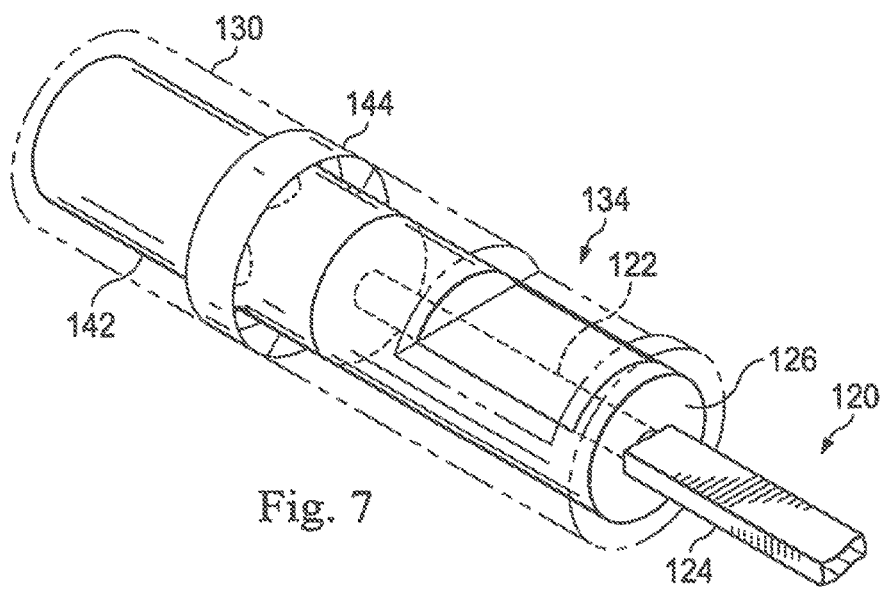

Referring now to FIG. 7, an annular band 144 is formed around a portion of the tubular member 130 according to an embodiment of the present disclosure. In that regard, the annular band 144 extends annularly around the tubular member 130 in alignment with the openings 140. In some embodiments, the annular band 144 is formed in a groove formed in the outer surface of the tubular member as discussed above. The annular band 144 is also a temporary structure that will be removed subsequently. Accordingly, the annular band 144 is formed of a material that can be chemically removed without damaging the tubular member 130, expander 126, and/or the proximal portion 122 of the distal core 120 in some instances. To that end, in some implementations the annular band 144 is formed of the same material as the temporary structure defined by material 142. For example, in some instances the annular band 144 could be formed of copper.

Figure 8:
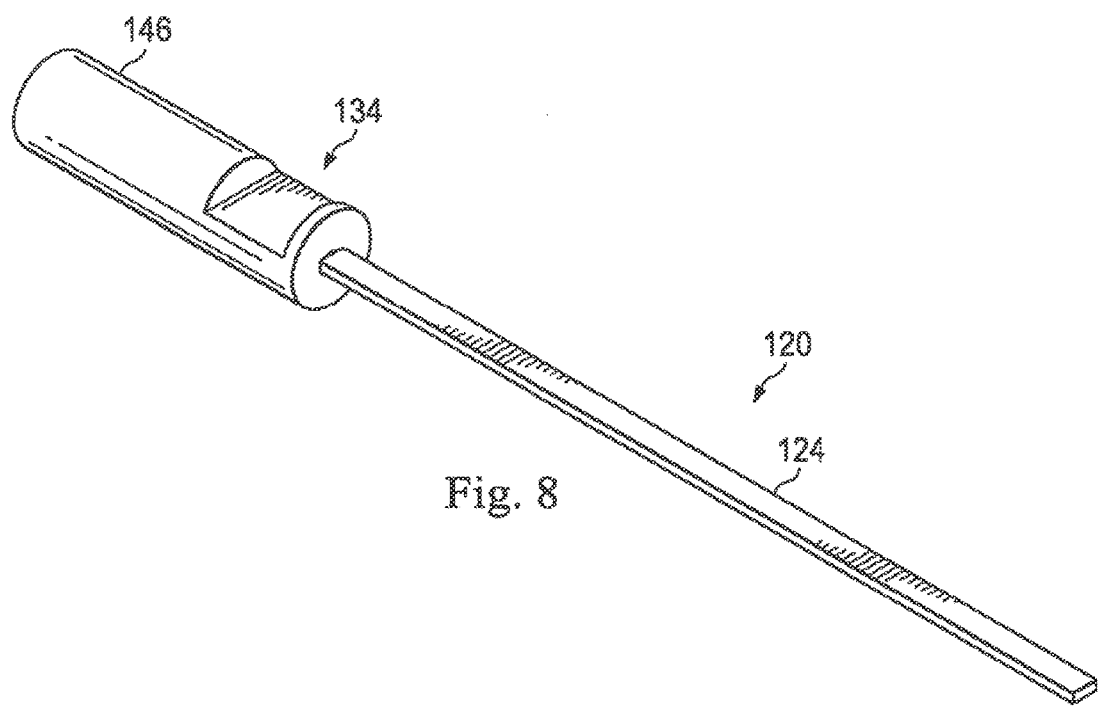

Referring now to FIG. 8, a material layer 146 is formed over the tubular member 130, expander 126, and proximal portion 122 of the distal core 120 according to an embodiment of the present disclosure. Generally, the material layer 146 is formed of a flexible material suitable to act as a membrane for a capacitive pressure sensing arrangement as will described in further detail below. Accordingly, in some instances the material layer 146 is formed of a flexible, non-conductive polymer material. In some embodiments, the material layer 146 is formed of parylene, PDMS (Polydimethylsiloxane), and/or combinations thereof. Further, the material layer 146 has a thickness between about 0.001 mm and about 0.003 mm in some instances. In the illustrated embodiment, the material layer 146 is parylene having a thickness of approximately 0.0013 mm. In some instances, the material layer 146 extends over the distal portion 124 of the distal core 120. In other instances, the distal portion 124 of the distal core 120 is masked and/or otherwise treated, protected, or avoided such that material layer 146 does not extend over the distal portion 124.

Figure 9:
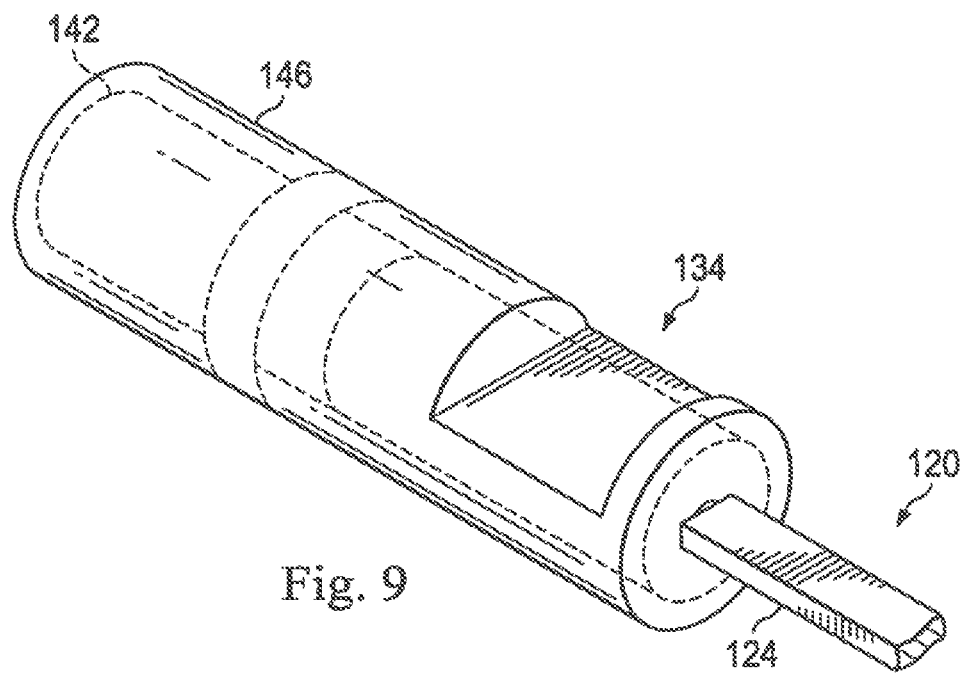

Referring now to FIG. 9, a section of the material layer 146 extending around the tubular member 130 and portions of the tubular member 130 are shown in phantom to reveal the presence of the temporary structure 142 and the temporary annular band 144 after formation of the material layer 146. With the material layer 146 formed, the temporary structure 142 and the temporary annular band 144 are chemically removed. In some embodiments, the temporary structure 142 and the temporary annular band 144 are removed immediately following formation of the material layer 146. In other embodiments, one or more additional steps are performed after formation of the material layer 146 before the temporary structure 142 and the temporary annular band 144 are removed. For example, in some instances the formation of the electrode described in the context of FIG. 14 is performed prior to removal of the temporary structure 142 and the temporary annular band 144.

Figure 10:
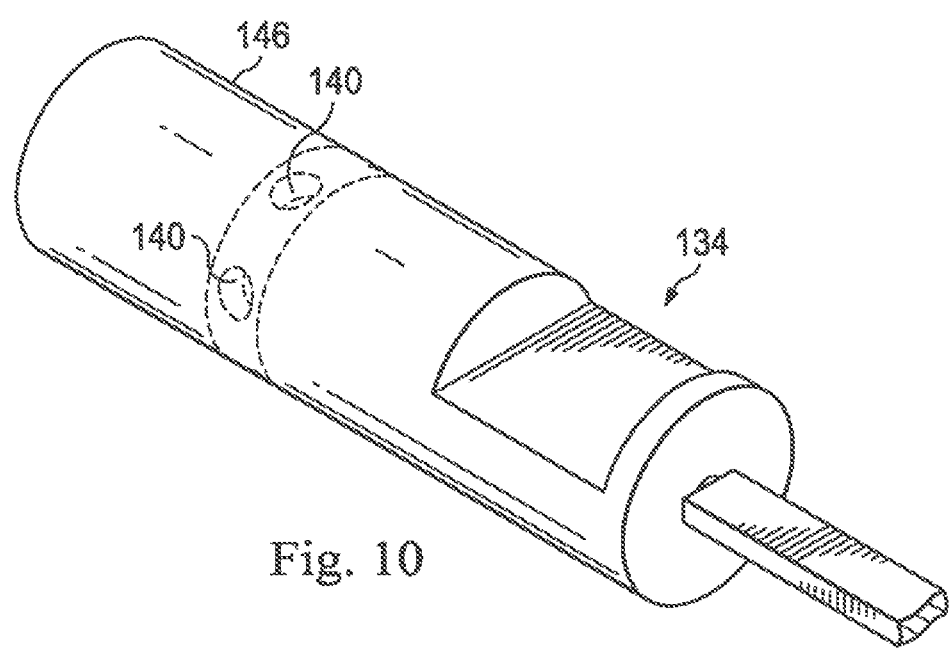
Figure 11:
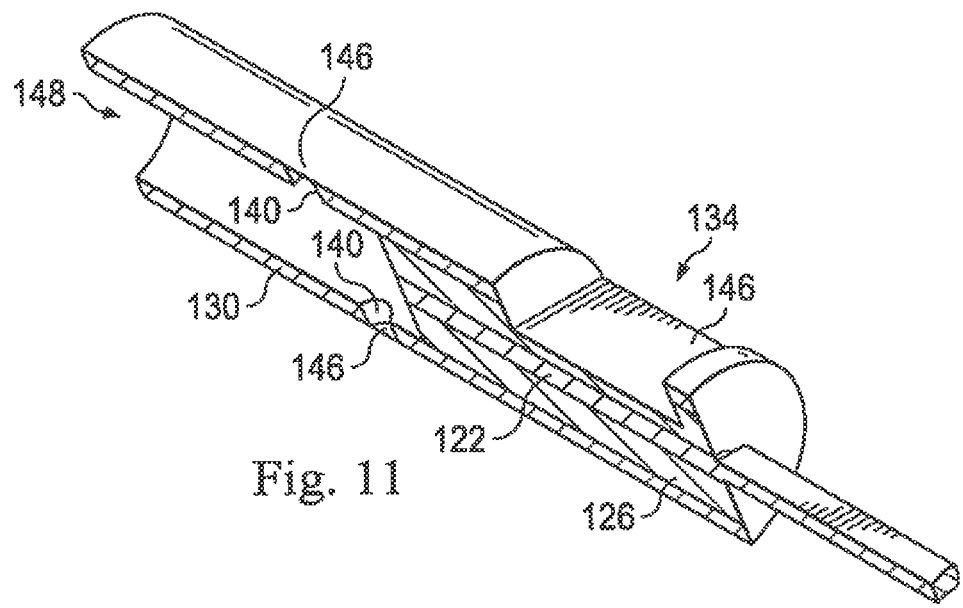
Figure 12:
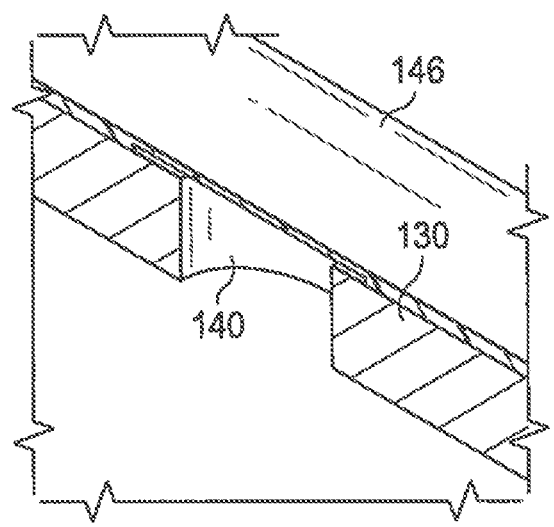

Referring now to FIGS. 10-12, the material layer 146, the tubular member 130, the expander 126, and the proximal portion 122 of the distal core 120 are shown after removal of the temporary structure 142 and the temporary annular band 144 according to an embodiment of the present disclosure. As best shown in FIGS. 11 and 12, with the temporary structure 142 and the temporary annular band 144 removed, the flexible material layer 146 is in communication with the central lumen 148 of the tubular member 130 via openings 140. Further, the sections of the material layer 146 positioned adjacent to the openings 140 are spaced from the outer wall of the tubular member 130 by a distance equal to the thickness of the temporary annular band 144 that was removed. This spacing allows the material layer 146 to flex in response to pressure changes.

Figure 13:
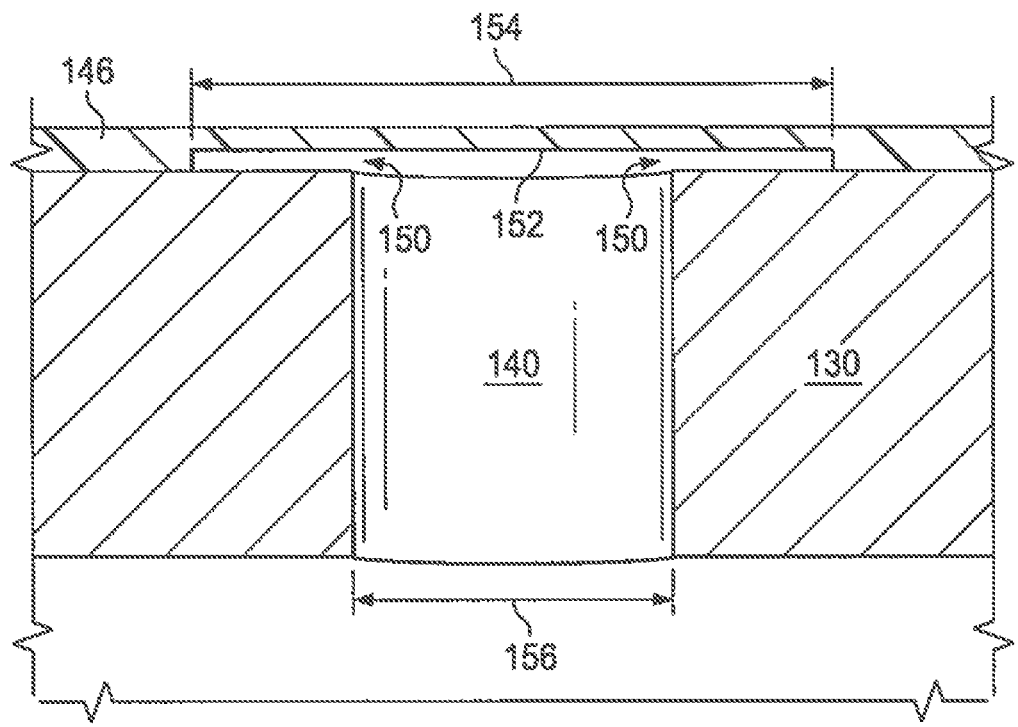

Referring to FIG. 13, a more detailed cross-sectional profile of the arrangement of the material layer 146 and tubular member 130 adjacent an opening 140 is shown. As illustrated, space 150 is provided between a lower surface 152 of the material layer 146 and the outer wall of the tubular member 130 adjacent the opening 140. As noted above, the space 150 is defined by the thickness of the annular band 144. In the illustrated embodiment, the annular band 144 had a width 154 that is greater than the diameter 156 of the opening 140. In some instances, the width 154 is between about 0.1 mm and about 0.2 mm, while the diameter 156 is between about 0.1 mm and about 0.2 mm. The space 150 facilitates flexing of the material layer 146 in response to pressure changes and, in particular, relative changes in pressure between the environmental pressure surrounding material layer 146 and an ambient (if vented) or sealed central lumen 148 of the tubular member 130. In some instances, the pressure within the central lumen 148 of the tubular member 130 is an atmospheric pressure. For example, in some instances the central lumen 148 is in communication with one or more additional lumens associated with the intravascular device that extend from the lumen 148 to an atmospheric pressure source. In other instances, the lumen 148 is sealed with a known and/or fixed pressure value.

Figure 14:
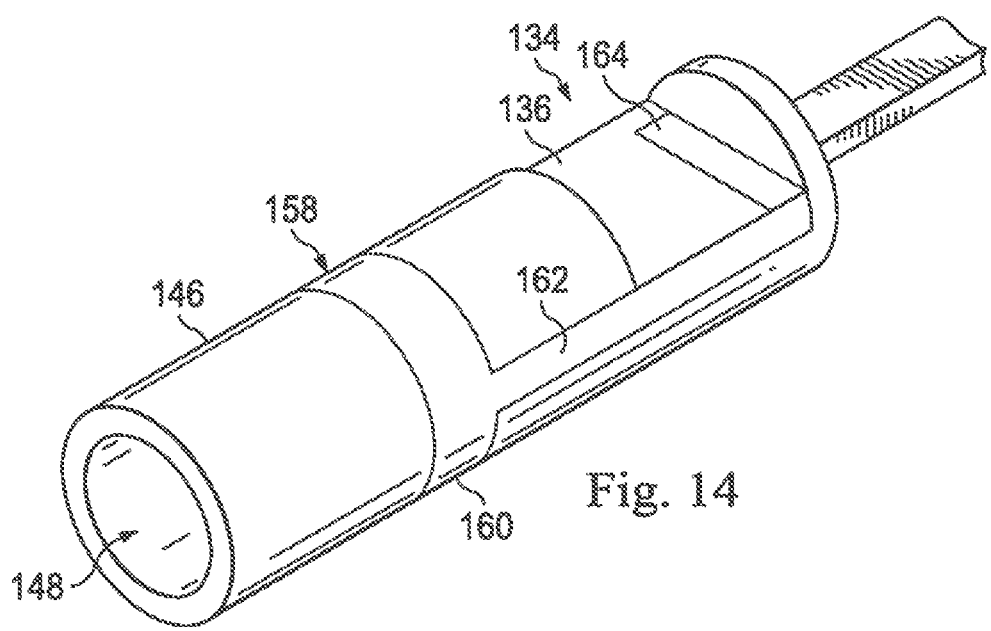

Referring now to FIG. 14, an electrode 158 has been formed over a portion of the material layer 146, and over the cavity formed by 144. The width of electrode 158 may be greater than groove width 154, equal to groove width 154, or less than groove width 154. In the illustrated embodiment, the width of 158 is greater than groove width 154. Electrode 158 is formed of a conductive material, such as gold (Au), titanium/gold alloy (Ti/Au), and/or other suitable conductive material, and may consist of one or multiple layers of identical or varied materials. The electrode 158 may be formed by additive or subtractive methods. These methods include, but are not limited to: aerosol jet printing, ink-jet printing, powder-metal fabrication, laser-direct sintering, plating-etching, plating-laser ablation, and/or other suitable technique. In the illustrated embodiment, the electrode 158 includes and is in electrical communication with, an annular portion 160 that extends around the tubular member 130, an axial portion 162 that extends along the major axis of the tubular member 130, and a pad portion 164 that extends across the distal-most region of mounting structure 134.

The annular portion 160 of the electrode 158 is fixedly attached to the outer surface of material layer 146 directly above the cavity formed by 144. In some embodiments, the annular portion 160 is centered on the cavity formed by 144, while in other embodiments, annular portion 160 is not centered on the cavity formed by 144. A capacitor is formed from the annular portion 160 (cathode), the material layer 146 (dielectric), and the structure formed from 120, 126, and 130 (anode). With sufficient difference between the pressure surrounding the cavity formed by 144 and the ambient or sealed cavity pressure, the suspended material layer 146 and annular portion 160 will deflect—creating a variable capacitor. To facilitate this capacitive pressure sensing operation, in some embodiments the annular portion 160 of electrode 158 is centered upon the openings 140 and extends around the circumference of the tubular member 130 between about 25% and about 100% of the total circumference of the tubular member. As shown in FIGS. 15-18, in the illustrated embodiment the annular portion 160 of electrode 158 extends around a majority of the circumference of the tubular member 130, but not completely around, such that a non-conductive section 166 of material layer 146 remains between the extents of annular portion 160. In other instances, annular portion 160 of electrode 158 extends completely around the circumference of the tubular member 130. In such instances, a dielectric patch or layer may be formed over a section of the annular portion 160 to define a non-conductive area similar to section 166.

The axial portion 162 of the electrode 158 extends between annular portion 160 and pad portion 164. In the illustrated embodiment, axial portion 162 of the electrode 158 is positioned on a side of the tubular member 130 substantially opposite section 166. The pad portion 164 of the electrode 158 defines a pad site for an ASIC component that will be subsequently mounted within the mounting structure 134. Accordingly, the axial portion 162 of the electrode 158 provides a conductive path between the annular portion 160 and the pad portion 164 such that changes in capacitance of the annular portion 160 can be conveyed to the ASIC component.

Figure 15:
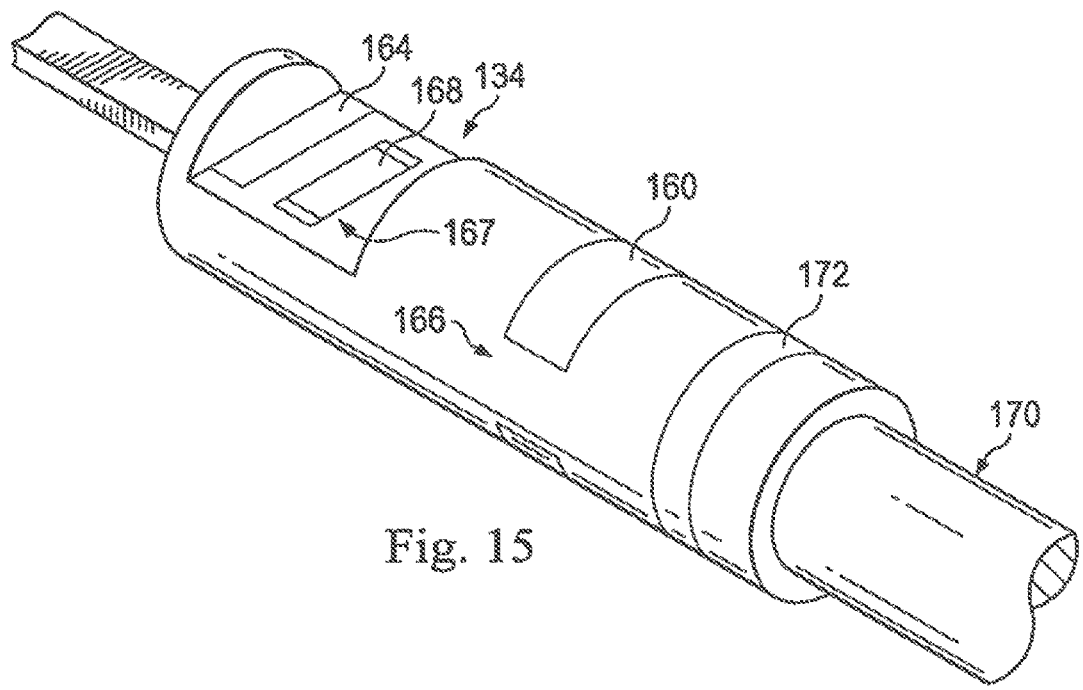

Referring now to FIG. 15, a section 167 of the material layer 146 within the mounting structure 134 has been removed (e.g., using laser ablation or other suitable technique) to expose a ground pad 168 on the expander 126 and proximal portion 122 of distal core 120. Section 168 defines a bond pad for the ASIC component that will be subsequently mounted within the mounting structure 134. Further, a flexible elongate member 170 is coupled to a proximal portion of the tubular member 130. In the illustrated embodiment, a distal portion of the flexible elongate member 170 is positioned within the lumen 148 of the tubular member 130. However, the distal portion of the flexible elongate member 170 is positioned within the lumen such that it is spaced proximally from the openings 140 in the tubular member 130 so as to not block the material layer 146 and annular portion 160 of the electrode 158 from having access to the lumen pressure through the openings 140. In some implementations, the lumen 148 of the tubular member 130 includes a counter bore, shoulder(s), and/or other suitable engagement structures to ensure that the distal portion of the flexible elongate member 170 is properly positioned within the tubular member 130 without blocking the openings 140.

In some implementations, the flexible elongate member 170 is a tubular member having a lumen extending along its length. To that end, the lumen of the flexible elongate member 170 is in communication with the lumen 148 of the tubular member 130 such that the lumen of the flexible elongate member 170, alone or in combination with other elements, can be used to expose the lumen 148 to a reference pressure source, such as atmospheric pressure and/or a known pressure value. In some embodiments, the flexible elongate member 170 is a solid wire and therefore does not reference atmospheric pressure. The flexible elongate member 170 may be formed of any suitable material, including without limitation stainless-steel, nitinol, optical fiber, ceramic, and/or other suitable material or combinations thereof. In some implementations, the flexible elongate member 170 is formed, at least partially, of conductive material. For example, in some instances the tubular member is formed of a non-conductive material coated with a conductive material. In such instances, all or only portions of the tubular member may be coated with the conductive material. The flexible elongate member 170 is fixedly secured to the tubular member 170 utilizing suitable techniques for the selected materials of the flexible elongate member 170 and the tubular member 130. Accordingly, in some instances the flexible elongate member 170 is fixedly secured to the tubular member 130 by solder, weld, adhesive, pressing, swaging, and/or combinations thereof. In the illustrated embodiment, the flexible elongate member 170 is formed of stainless-steel and is laser welded to tubular member 130 as indicated by weld line 172. In the illustrated embodiment the flexible elongate member 170 is electrically coupled to the tubular member 130. In some implementations, the elongate member 170, tubular member 130, and associated electrically coupled portions of the device carry a ground signal.

In some instances, the flexible elongate member 170 includes an outer insulating coating (e.g., a parylene layer or other suitable insulating material) along a majority of its length. In some instances, the insulating coating is applied after the flexible elongate member 170 is coupled to the tubular member 130. In other instances, the insulating coating is applied prior to the flexible elongate member 170 being coupled to the tubular member 130. To that end, in some instances one or more sections of the flexible elongate member 170 are masked, treated, and/or avoided to prevent application of the insulating coating. For example, the section of the flexible elongate member 170 that is welded to the tubular member 130 may not include an insulating coating after the procedure, and/or a proximal section of the flexible elongate member 170 that is used to define an electrical connector (or be coupled to an electrical connector) may not include an insulating coating. Alternatively, in some instances an insulating coating is applied to the entire flexible elongate member 170 and then sections of the insulating coating are removed, as necessary, to expose underlying portions of the flexible elongate member 170.

Figure 16:
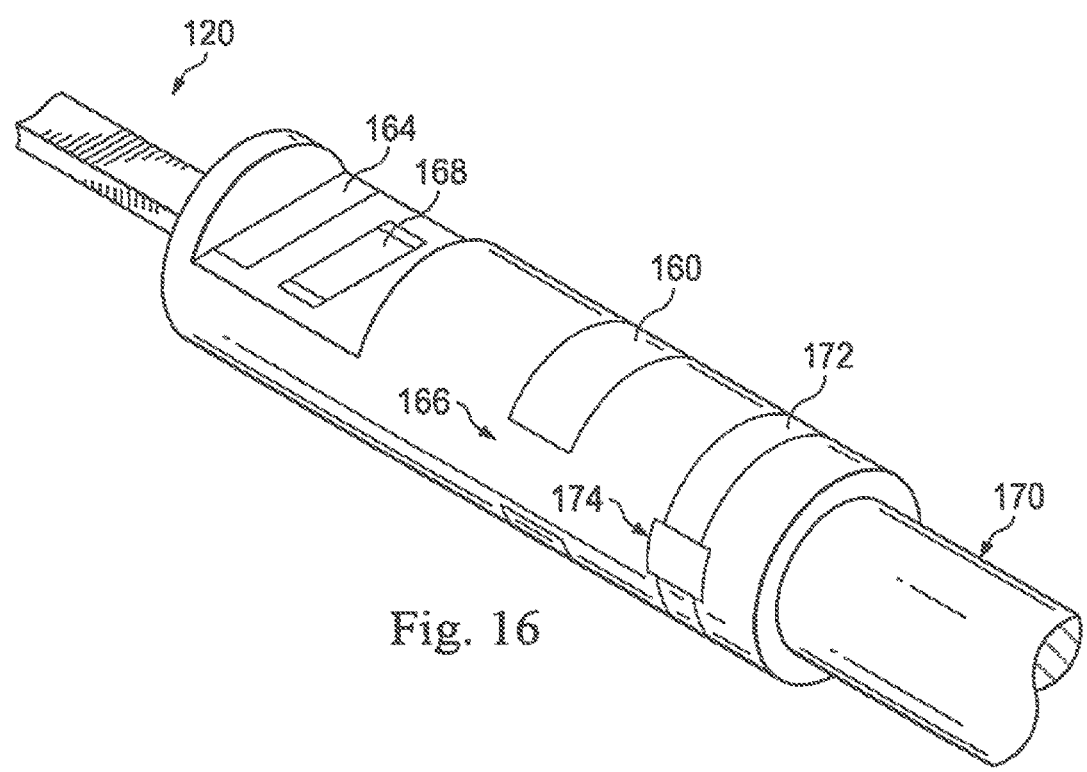

Referring now to FIG. 16, a dielectric patch 174 is formed over the weld line 172. As shown, the dielectric patch 174 is generally aligned with the section 166 of material layer 146 separating the ends of the annular portion 160 of the electrode 158. For embodiments where the annular portion 160 of the electrode 158 extends completely around the tubular member 130, the dielectric patch 174 can extend across both the weld line 172 and the annular portion 160. Alternatively, two different dielectric patches could be formed across the weld line 172 and the annular portion 160, respectively, for embodiments where the annular portion 160 of the electrode 158 extends completely around the tubular member 130. The dielectric patch can be formed of any suitable dielectric material such as Parylene, PDMS, or other suitable dielectric material. The dielectric patch 174 and section 166 serve to electrically isolate an electrode 176 (See, FIG. 17) from the electrode 158 and the tubular member 130.

Figure 17:
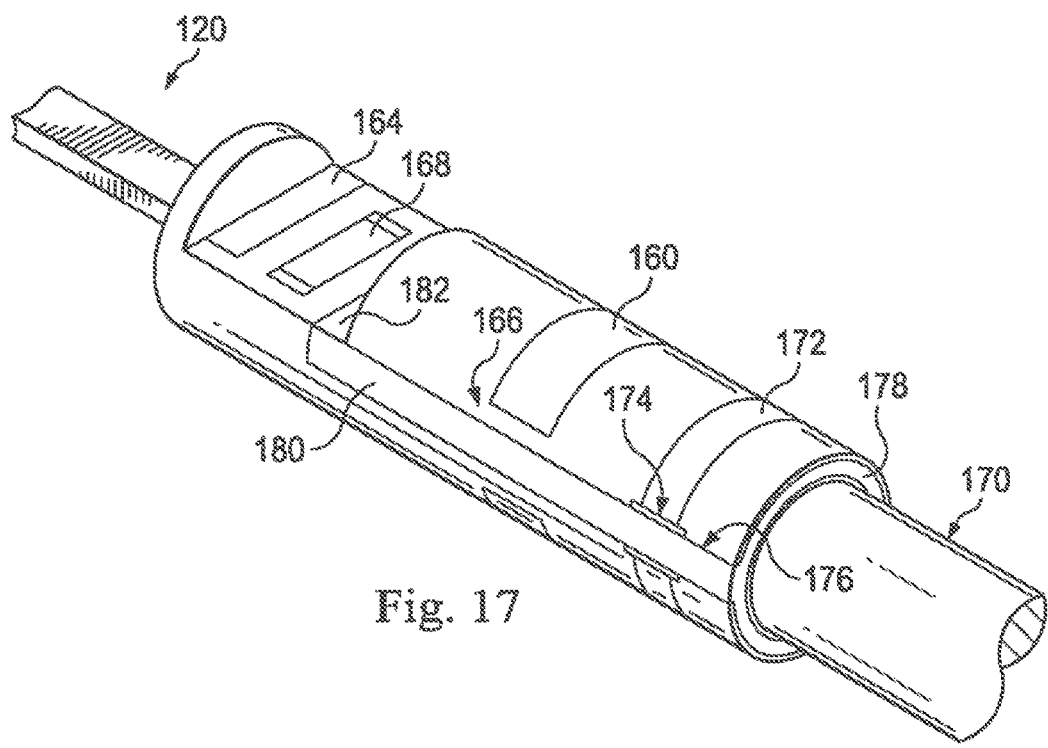

Referring now to FIG. 17, an electrode 176 has been formed over a portion of the material layer 146 surrounding the tubular member 130 according to an embodiment of the present disclosure. The electrode 176 is formed of a conductive material, such as gold (Au), titanium/gold alloy (Ti/Au), and/or other suitable conductive material, and may consist of one or multiple layers of identical or varied materials. The electrode 176 may be formed by additive or subtractive methods. These methods include, but are not limited to: aerosol jet printing, ink-jet printing, powder-metal fabrication, laser-direct sintering, plating-etching, plating-laser ablation, etc. In the illustrated embodiment, the electrode 176 includes and is in electrical communication with, a ring pad 178 that is formed on the proximal end of tubular member 130, an axial portion 180 that extends along the major axis of the tubular member 130, and a pad portion 182 that extends across the proximal-most region of mounting structure 134.

The ring pad 178 of the electrode 176 extends around the circumference of the tubular member 130 between about 25% and about 100% of the total circumference of the flexible elongate member 170. In the illustrated embodiment, the ring pad 178 of electrode 176 extends completely around the circumference of the flexible elongate member 170. The axial portion 180 of the electrode 176 extends between ring pad 178 and pad portion 182. In the illustrated embodiment, axial portion 180 of the electrode 176 is positioned on a side of the tubular member 130 substantially opposite axial portion 162 of electrode 158. To that end, the axial portion 180 extends across dielectric patch 174 and section 166 of the material layer 146 such that the electrode 176 is electrically isolated from the electrode 158 and the tubular member 130. The pad portion 182 of the electrode 176 defines a further pad site for the ASIC component that will be subsequently mounted within the mounting structure 134. Accordingly, the pad portion 182 of the electrode 176 provides a conductive path between the ring pad 178 and the pad portion 182.

Figure 18:
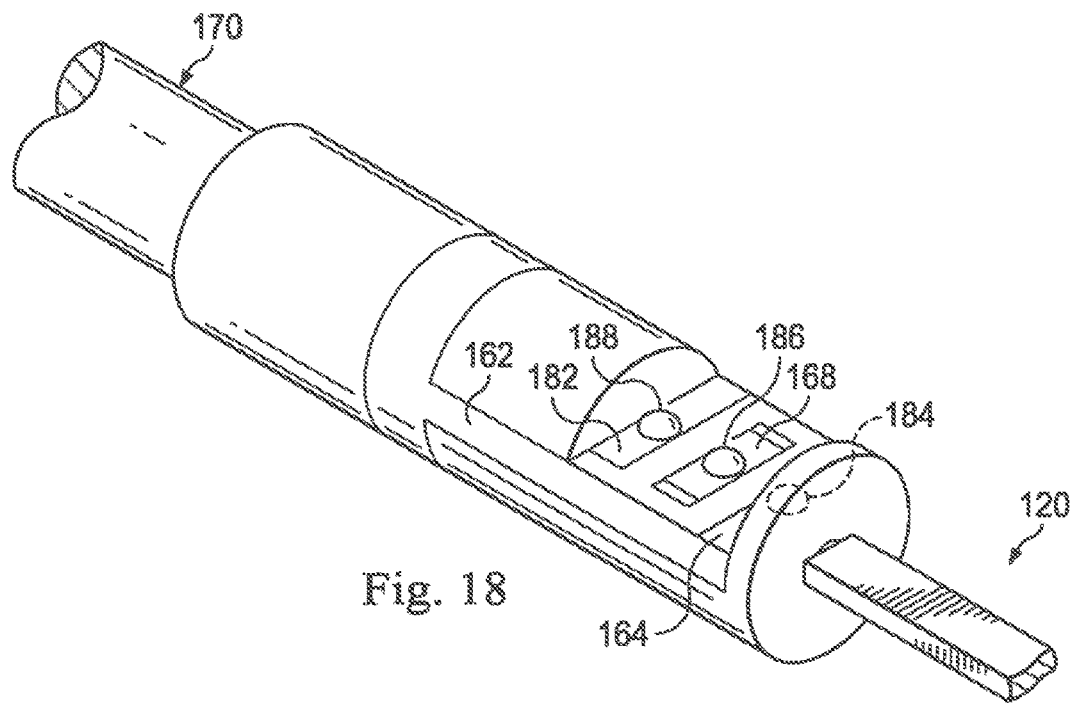

Referring now to FIG. 18, a conductive material (e. g. conductive adhesive, conductive film, solder paste, solder balls, etc.) is applied to the pad sites on mounting structure 134. In the illustrated embodiment, conductive adhesive is applied to pad portion 164 of electrode 158, ground pad 168 on expander 126, and pad portion 182 of electrode 176 to facilitate mounting of an ASIC within the mounting structure 134 such that the ASIC is electrically coupled to the pad sites. As shown, adhesive 184 is applied to pad portion 164 of electrode 158, adhesive 186 is applied to ground pad 168 on expander 126, and adhesive 188 is applied to pad portion 182 of electrode 176. Generally, any suitable conductive adhesive may be utilized. In some instances, the adhesive is silver-epoxy.

Figure 19:
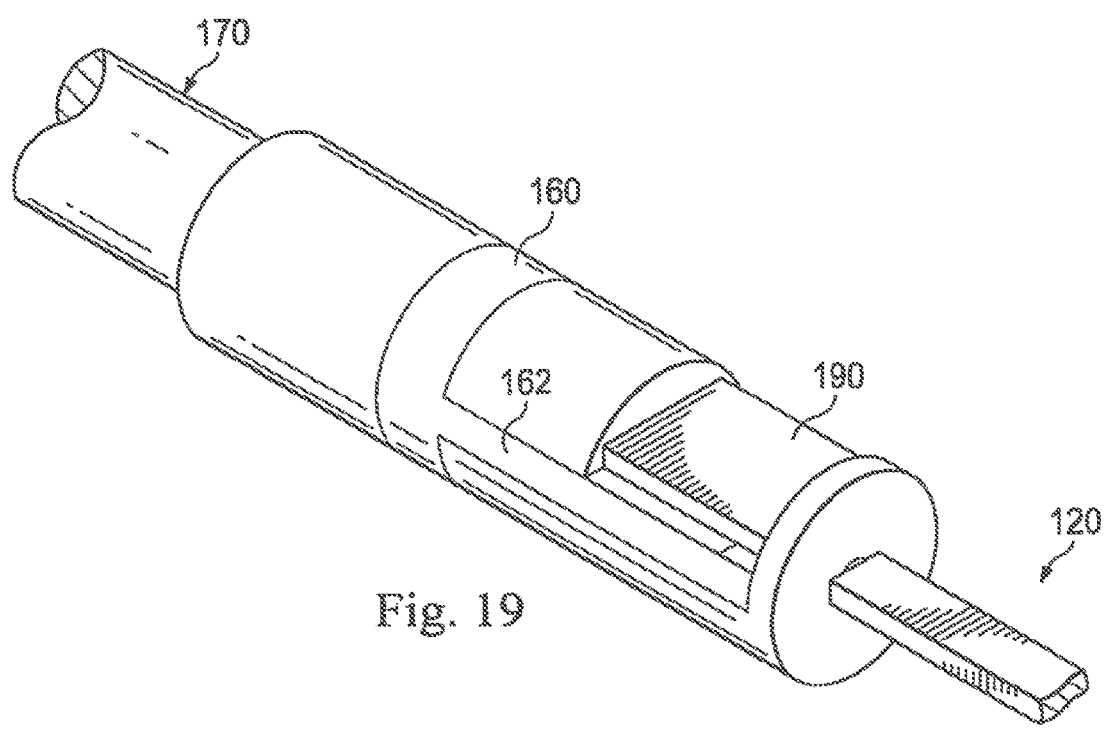

Referring now to FIG. 19, an ASIC module 190 has been mounted within the mounting structure 134 and electrically coupled to pad portion 164 of electrode 158, ground pad 168 on expander 126, and pad portion 182 of electrode 176 by the conductive adhesives 184, 186, 188, respectively. In some instances, the ASIC module 190 may be one or more components and may include one, several, or all of the capabilities related to memory storage, signal conditioning, wireless communication interface, etc. The memory element may store information about the characteristics and use of the sensor. In some instances, the memory element stores device-specific information such as: device ID, usage limit, sensor ID, temperature coefficient, zero offset, scale factor, sensitivity, manufacture date, manufacture time, and manufacture location. In addition, the memory element may store information related to one or more specific periods of device activation or use, such as: count, date, time, location, system ID, pressure minimum, pressure maximum, velocity minimum, velocity maximum, temperature minimum, temperature maximum, and centered (y/n). The ASIC module 190 is energized via VCC from pad portion 164 and ground from ground pad 168. With the ASIC module 190 mounted within the mounting structure 134, the spacing around the ASIC module 190 can be filled in using under-filling and/or over-molding to further secure the ASIC module 190 in place and/or return the outer profile of the device to a cylindrical form such that it has generally constant outer profile along the length of the tubular member 130.

Figure 20:
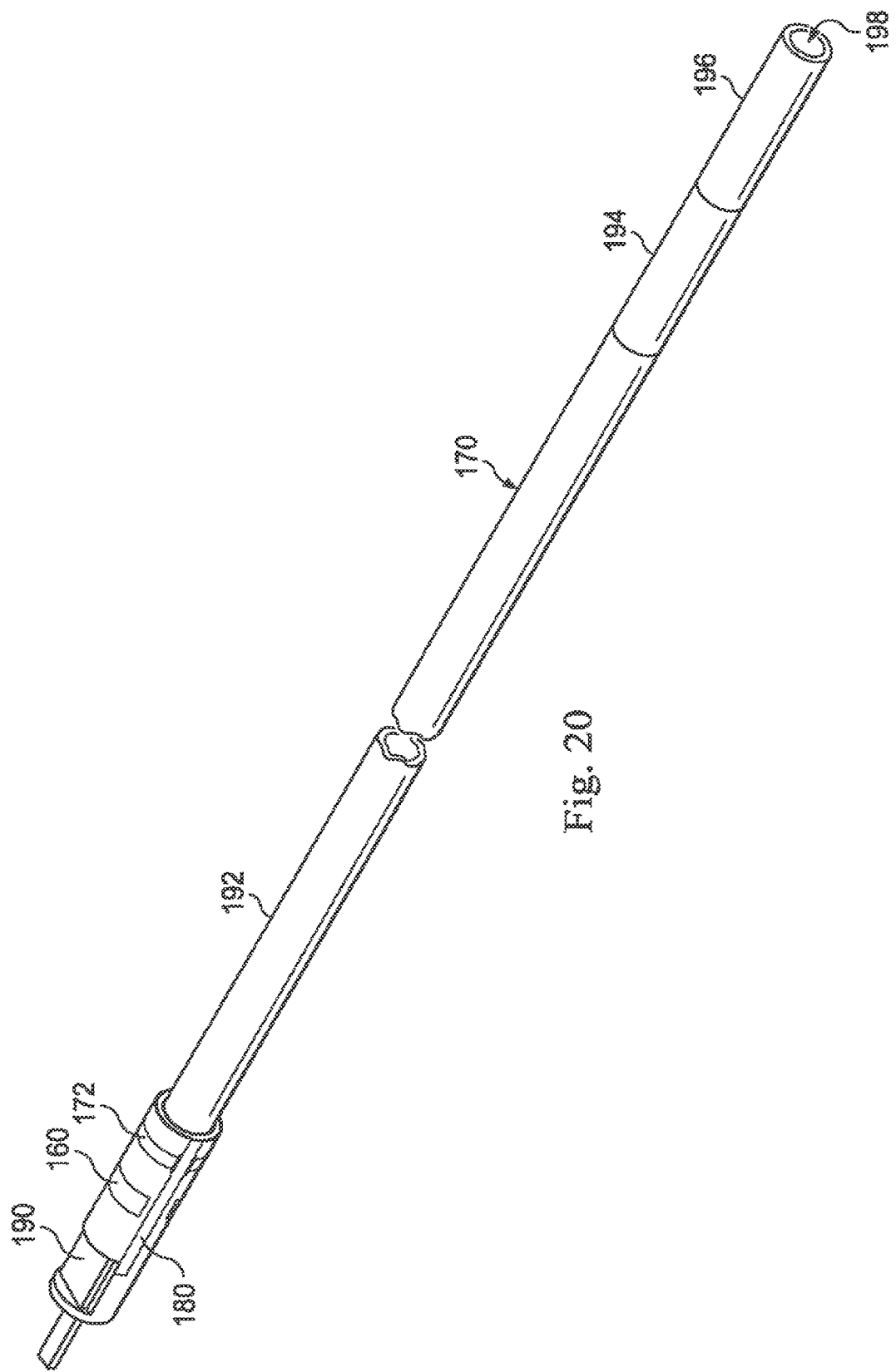

Referring now to FIG. 20, a conductive layer 192 is formed over the material layer 146 such that the conductive layer covers all but an insulating band portion 194 at the proximal-most portion of insulating material layer 146. As shown, the proximal-most portion of insulating material layer 146 defining insulating band portion 194 is spaced from the proximal-most portion of flexible elongate member 170 such that a conductive band 196 is defined. As discussed above, in some instances the flexible elongate member 170 serves as a ground source such that the conductive band 196 is a ground band. FIG. 20 also illustrates an opening to the lumen 198 of the flexible elongate member 170 at the proximal end of the flexible elongate member 170. In some instances, the material layer 146 defining insulating band portion 194 and/or the conductive layer 192 of the flexible elongate member 170 are formed prior to the assembly of the flexible elongate member with any other components of the intravascular device. In this manner, the flexible elongate member 170 may be a separate sub-assembly to streamline manufacturing procedures.

Figure 21:
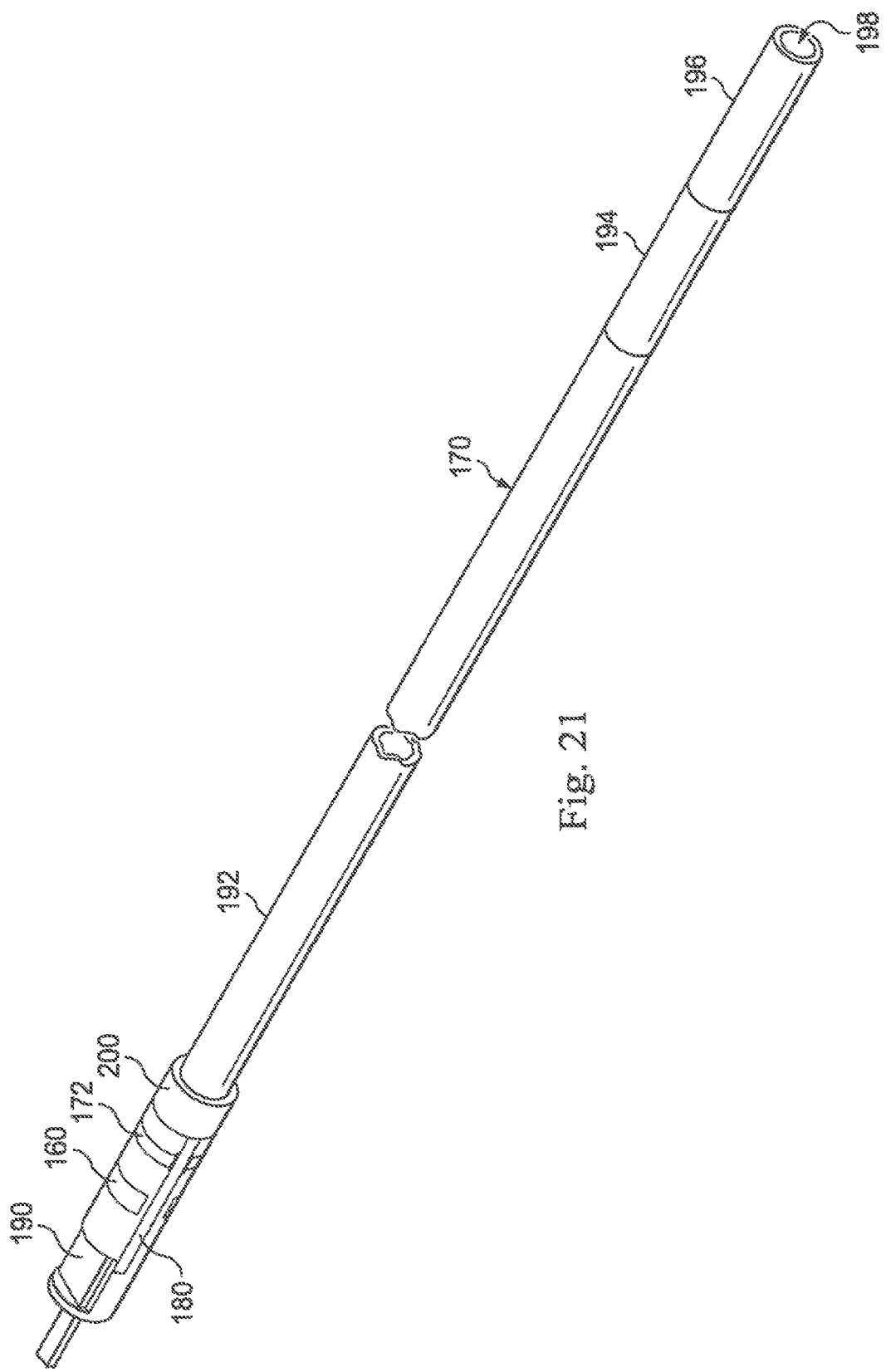

Referring now to FIG. 21, a conductive spacer 200 is positioned around the distal portion of the flexible elongate member 170 adjacent to the proximal end of the tubular member 130. In that regard, the conductive spacer includes a conductive material on at least its distal end surface to electrically couple to the ring pad 178 of electrode 176 and its inner surface to electrically couple to the conductive layer 192. An electrically conductive adhesive (such as silver-epoxy) is utilized in some instances to secure the conductive spacer 200 to the electrode 176 and/or the conductive layer 192. In other instances, the conductive spacer 200 is electrically coupled and secured to the electrode 176 and/or the conductive layer 192 using conductive film. In an alternate embodiment, ring pad 178 and conductive layer 192 are direct-printed as one continuous, and electrically connected structure.

Figure 22:
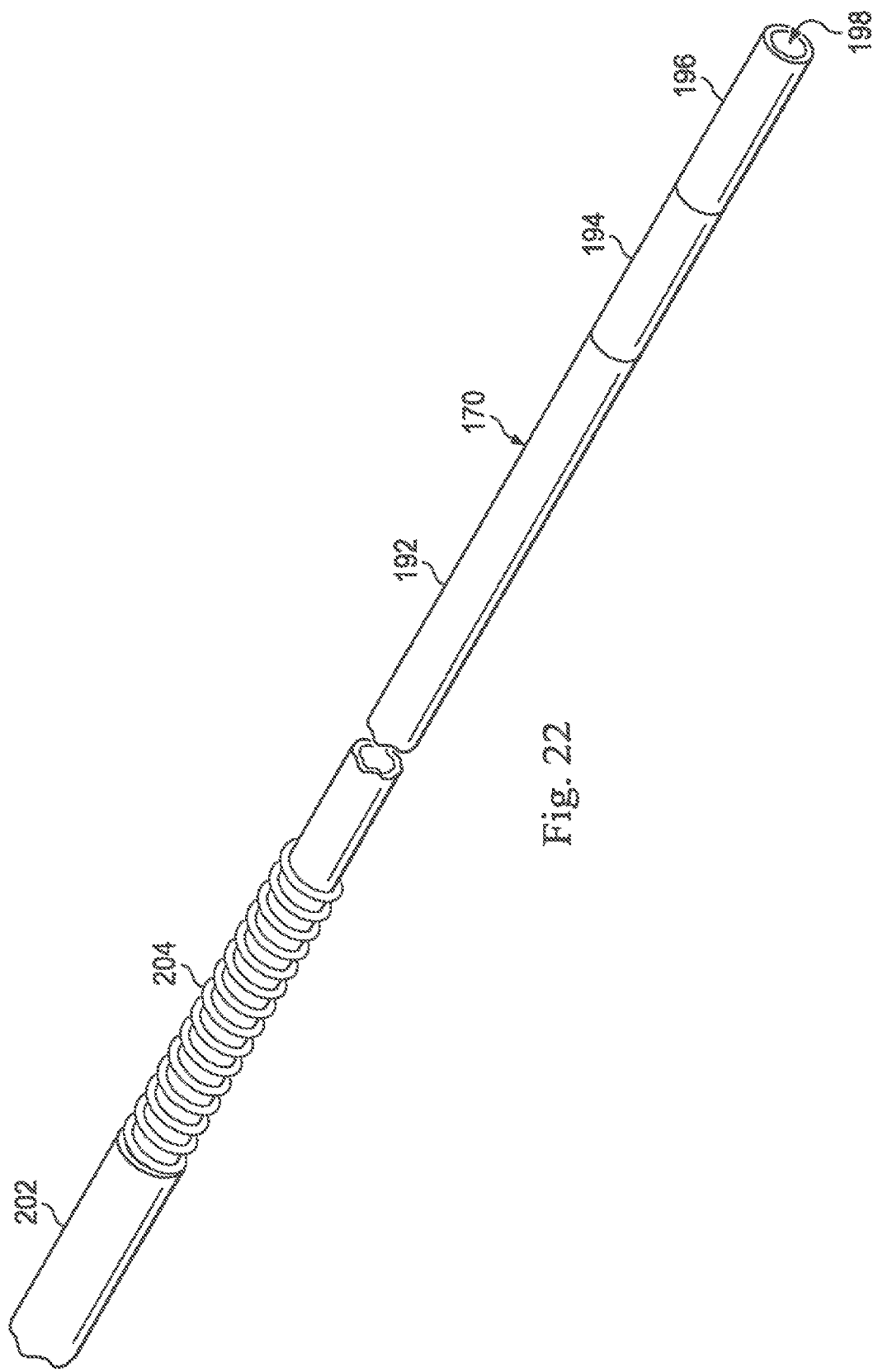

Referring now to FIG. 22, a flexible element 204 is positioned around a distal portion of the flexible elongate member 170 adjacent to the conductive spacer 200. In particular, a distal end of the flexible element 204 abuts a proximal end of the conductive spacer 200. In some embodiments, the outer-diameter of the conductive spacer 200 is smaller than the inner-diameter of the flexible element 204 or contains external threads or protrusions that allow the flexible element 204 to slide or thread onto the conductive spacer 200. The flexible element 200 is fixed to the conductive spacer 200 with a suitable adhesive. The flexible element 204 is similar to the proximal flexible element 109 discussed in the context of FIG. 1. Further, the flexible element 204 has a generally cylindrical outer profile and, therefore, further expands the radial diameter of the flexible elongate member 170. To that end, in some instances the flexible element 204 has an outer diameter generally equal to the sensor region 202 (about 0.36 mm).

Similarly, in a previous or subsequent step, another flexible element is positioned around the distal portion 124 of the distal core 120 in a manner similar to the distal flexible element 110 discussed in the context of FIG. 1. This distal flexible element also has a generally cylindrical outer profile and, therefore, further expands the radial diameter of the distal portion 124 of the distal core 120. To that end, in some instances the distal flexible element 110 has an outer diameter generally equal to the sensor region 202 (about 0.36 mm). In the illustrated embodiment, the distal-most tip 105 of the distal flexible element 110 is radiopaque. The radiopaque tip is generally round to facilitate navigation while minimizing tissue damage while manipulating the intravascular device through the vasculature.

Figure 23:
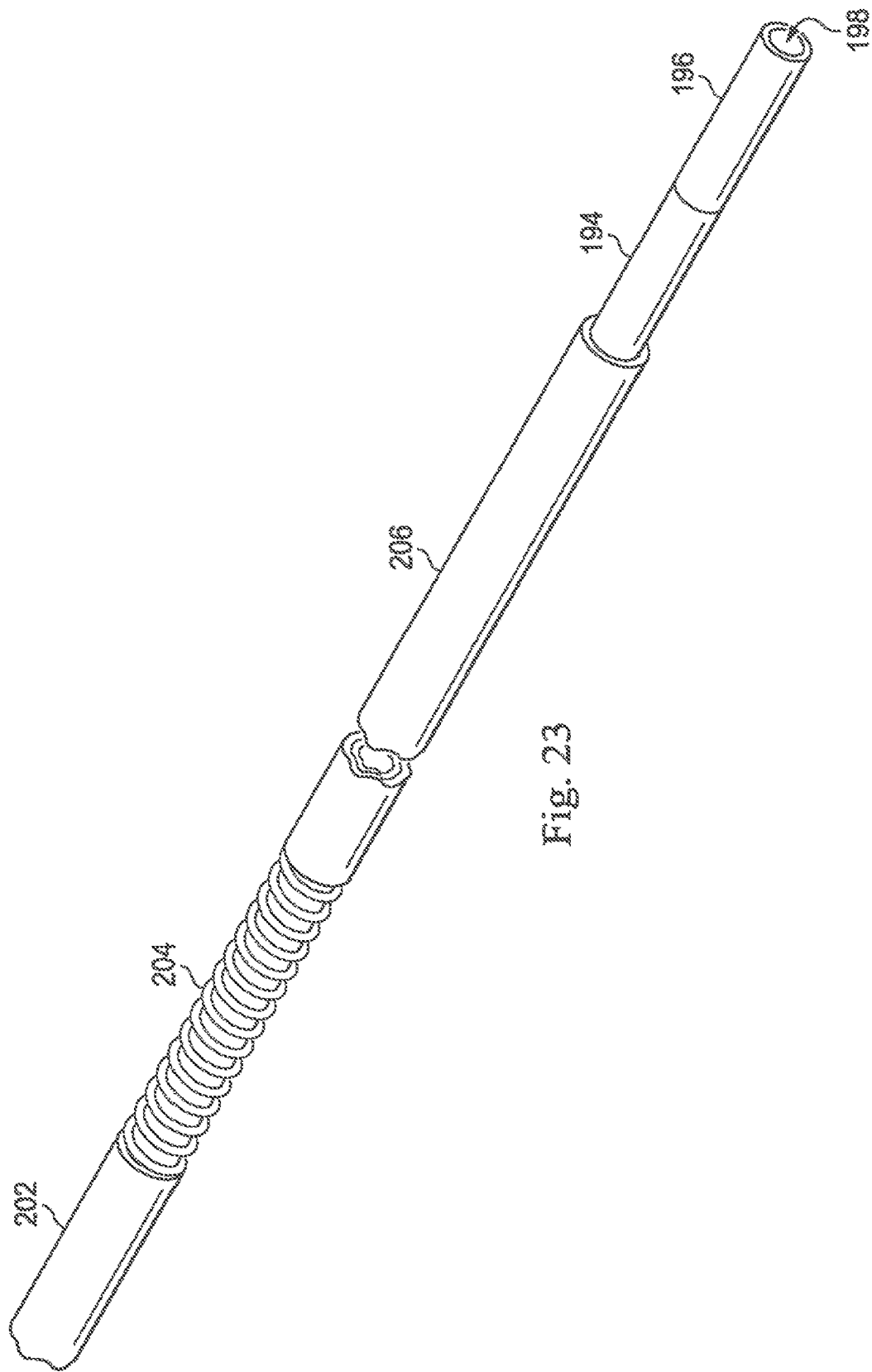

Referring now to FIG. 23, a conductive tubular member 206 is positioned over the conductive layer 192 of the flexible elongate member 170. As shown, a distal end of the conductive tubular member 206 abuts a proximal end of the flexible element 204, while a proximal end of the conductive tubular member 206 terminates adjacent to the insulating band portion 194 of the flexible elongate member 170. Further, the conductive tubular member 206 has a generally cylindrical outer profile and, therefore, further expands the radial diameter of the flexible elongate member 170. To that end, in some instances the conductive tubular member 206 has an outer generally equal to the sensor region 202 (about 0.36 mm).

The conductive tubular member 206 may be formed of any suitable conductive material, including without limitation stainless-steel, nitinol, and/or other suitable conductive material. In some implementations, conductive tubular member 206 is formed of a non-conductive material, then coated/plated with a conductive material. In such instances, all or only portions of the tubular member may be coated with the conductive material. The conductive tubular member 206 is fixedly secured and electrically coupled to the conductive layer 192 of the flexible elongate member 170 utilizing suitable techniques for the selected materials of the conductive tubular member 206 and the conductive layer 192. Accordingly, in some instances the conductive tubular member 206 is fixedly secured to the flexible elongate member 170 by conductive adhesive, swaging and/or combinations thereof. In the illustrated embodiment, the conductive tubular member 206 is formed of stainless-steel and is coupled to the flexible elongate member 170 by conductive adhesive. Thus, in the illustrated embodiment the conductive tubular member 206 is electrically coupled to the conductive layer 192, the conductive spacer 200, and the electrode 176.

Figure 24:
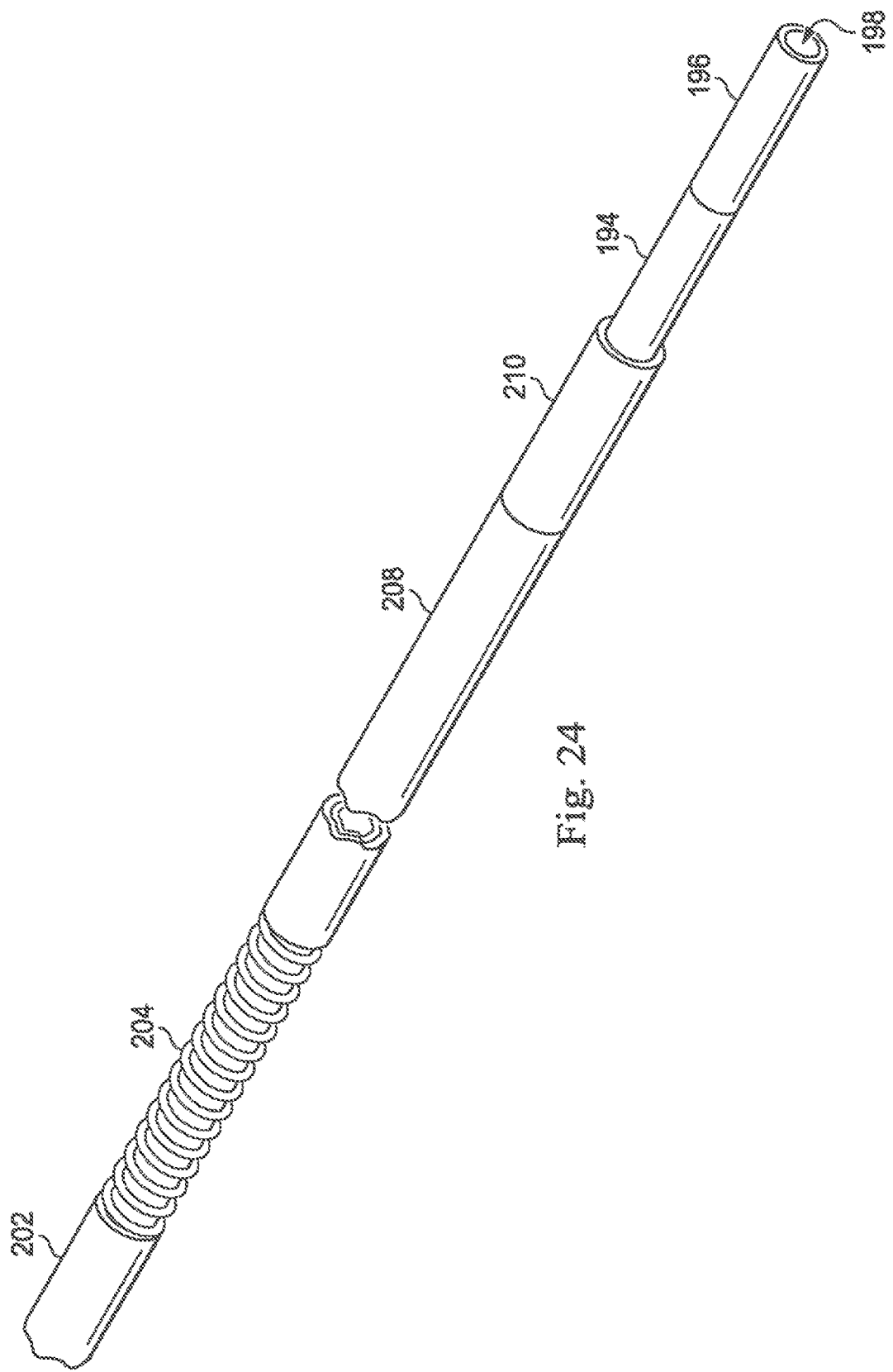

Referring now to FIG. 24, an insulating layer 208 is formed over the conductive tubular member 206 along a majority of the length of the conductive tubular member. In some instances, the insulating coating is applied after the conductive tubular member 206 is coupled to the conductive layer 192 of flexible elongate member 170. In other instances, the insulating layer 208 is applied prior to the conductive tubular member 206 being coupled to the flexible elongate member 170. To that end, in some instances one or more sections of the conductive tubular member 206 are masked, treated, and/or avoided to prevent application of the insulating coating. For example, in the illustrated embodiment the insulating layer 208 does not extend over a section 210 at the proximal end of the conductive tubular member 206. In that regard, in some implementations the section 210 defines an electrical connector similar to conductive band 114 of connector 111 discussed in the context of FIG. 1. Alternatively, in some instances the insulating coating is applied to the entire conductive tubular member 206 and then sections of the insulating coating are removed, as necessary, to expose underlying portions of the conductive tubular member 206.

Figure 25:
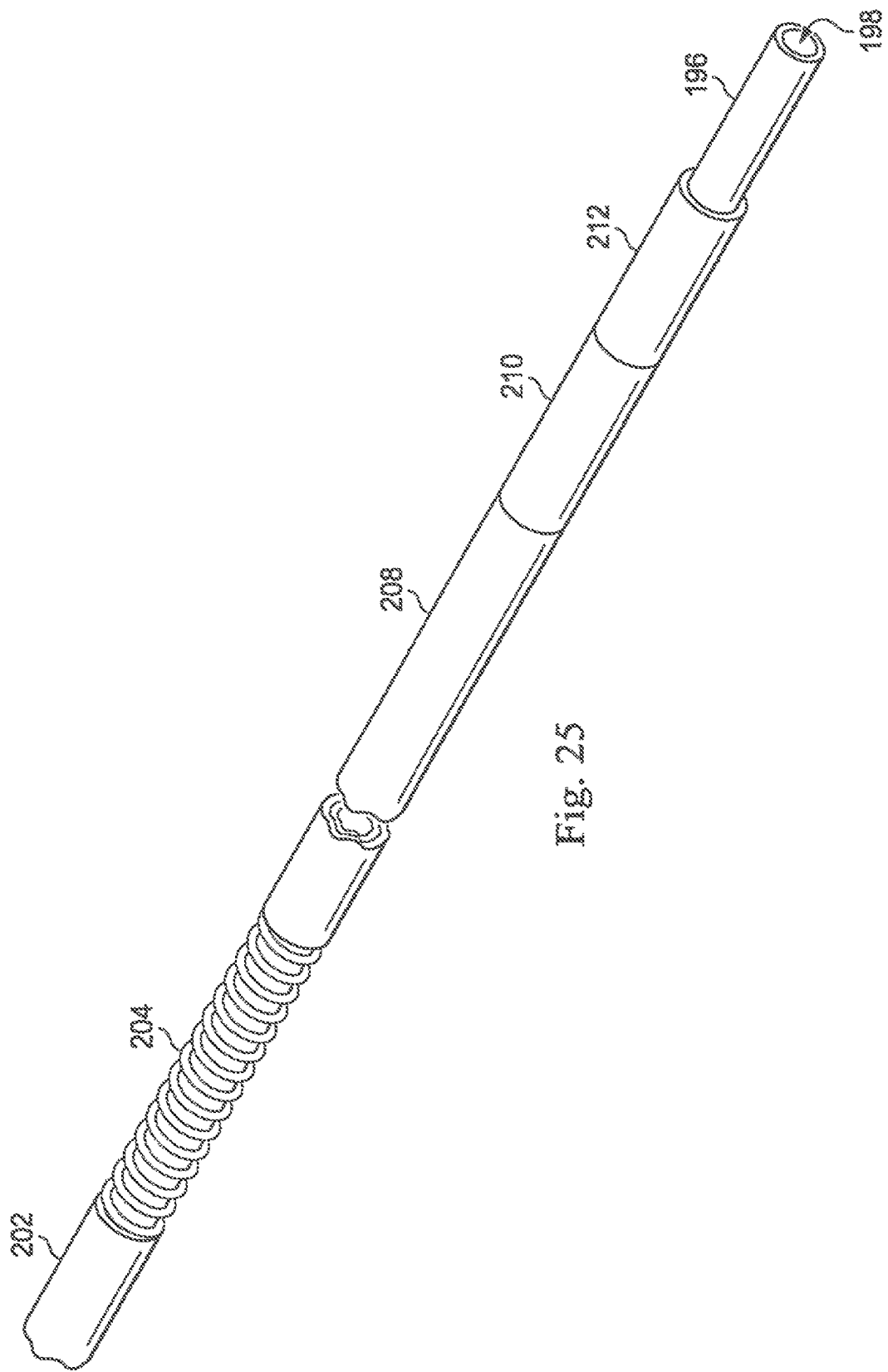

Referring now to FIG. 25, an insulating spacer 212 is positioned over insulating band portion 194 of the flexible elongate member 170 according to an embodiment of the present disclosure. As shown, a distal end of the insulating spacer 212 abuts a proximal end of the conductive tubular member 206, while a proximal end of the insulating spacer 212 terminates adjacent to the distal extent of ground band 196 of the flexible elongate member 170. The insulating spacer 212 has a generally cylindrical outer profile and, therefore, further expands the radial diameter of the flexible elongate member 170. To that end, in some instances the insulating spacer 212 has an outer diameter generally equal to the sensor region 202 (about 0.36 mm). The insulating spacer 212 may be formed of any suitable insulating material, including without limitation PP/PE/PA/PC/ABS. The insulating spacer 212 is fixedly secured to the flexible elongate member 170 utilizing suitable techniques for the selected materials of the insulating spacer 212 and the insulating material of insulating band portion 194 of the flexible elongate member 170. Accordingly, in some instances the insulating spacer 212 is fixedly secured to the flexible elongate member 170 by an adhesive. In other instances, the insulating spacer 212 is not itself fixedly secured to the flexible elongate member, but is positioned between components that are fixedly secured, such as conductive tubular member 206 and conductive sleeve 214 (See, FIG. 26). In the illustrated embodiment, the insulating spacer 212 is formed of PP and is not fixedly coupled to insulating band portion 194 on the flexible elongate member 170.

Referring now to FIGS. 26 and 27, a conductive sleeve 214 is positioned over ground band 196 at the proximal extent of flexible elongate member 170. As shown, a distal end of the conductive sleeve 214 abuts a proximal end of the insulating spacer 212, while a proximal end of the conductive sleeve 214 terminates adjacent to proximal end of the flexible elongate member 170. Further, the conductive sleeve 214 has a generally cylindrical outer profile and, therefore, further expands the radial diameter of the flexible elongate member 170. To that end, in some instances the conductive sleeve 214 has an outer diameter generally equal to the sensor region 202 (about 0.36 mm).

The conductive sleeve 214 may be formed of any suitable conductive material, including without limitation gold (Au), titanium-gold (Ti/Au), platinum-iridium (PtIr), and/or other suitable conductive material. In some implementations, conductive sleeve 214 is formed of a non-conductive material then coated with a conductive material. In such instances, all or only portions of the tubular member may be coated with the conductive material. The conductive sleeve 214 is fixedly secured and electrically coupled to the conductive ground band 196 of the flexible elongate member 170 utilizing suitable techniques for the selected materials of the conductive sleeve 214 and the conductive ground band 196 of the flexible elongate member 170. Accordingly, in some instances the conductive sleeve 214 is fixedly secured to the flexible elongate member 170 by solder, weld, conductive adhesive, pressing, swaging, and/or combinations thereof. In the illustrated embodiment, the conductive sleeve 214 is formed of PtIr and is coupled to ground band 196 of the flexible elongate member 170 by swaging. Thus, in the illustrated embodiment the conductive sleeve 214 is electrically coupled to the flexible elongate member 170, tubular member 130, and extender 126, which is electrically coupled to the ASIC module 190 via ground pad 168.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular pressure-sensing apparatus, comprising:
    a first elongate flexible element comprising a proximal portion and a distal portion, the first elongate flexible element being formed of a conductive material;
    a cylindrically-shaped housing at a distal portion of the first elongate flexible element, the housing comprising:
        a capacitive pressure sensing structure comprising a flexible membrane positioned around at least a portion of a cavity and a conductive member positioned around at least a portion of the flexible membrane such that the conductive member is displaced by changes in ambient pressure relative to a pressure in the cavity; and
        an application-specific integrated circuit (ASIC) in electrical communication with the conductive member of the capacitive pressure sensing component and the first elongate flexible element.

2. The apparatus of claim 1, wherein the cavity comprises a lumen of the housing.

3. The apparatus of claim 2, wherein the housing includes a plurality of openings in a sidewall of the housing, the plurality of openings in communication with the lumen.

4. The apparatus of claim 3, wherein the plurality of openings are formed radially around a circumference of the housing.

5. The apparatus of claim 1, wherein a section of the proximal portion of the first elongate flexible element is electrically coupled to a first conductive band.

6. The apparatus of claim 5, further comprising:
    a second elongate flexible element positioned around the first elongate flexible element, the second elongate flexible element being formed of a conductive material.

7. The apparatus of claim 6, wherein a section of a proximal portion of the second elongate flexible element defines a second conductive band.

8. The apparatus of claim 7, wherein the first conductive band is positioned proximal of the second conductive band.

9. The apparatus of claim 7, further comprising an insulating member positioned between the first and second conductive bands, the insulating member being positioned around the first elongate flexible element.

10. The apparatus of claim 6, wherein a majority of the second elongate flexible element is electrically isolated from the first elongate flexible element by a non-conductive layer covering the first elongate flexible element.

11. The apparatus of claim 6, wherein an outer diameter of the second elongate flexible element is 0.018" or less.

12. The apparatus of claim 6, wherein the outer diameter of the second elongate flexible element is 0.014" or less.

13. An intravascular pressure-sensing system, the system comprising:
    a pressure-sensing apparatus, comprising:
        an elongate flexible element comprising a proximal portion and a distal portion, the elongate flexible element being formed of a conductive material;
        a cylindrically-shaped housing at a distal portion of the elongate flexible element, the housing comprising:

a capacitive pressure sensing structure comprising a flexible membrane positioned around at least a portion of a cavity and a conductive member positioned around at least a portion of the flexible membrane such that the conductive member is displaced by changes in ambient pressure relative to a pressure in the cavity; and an application-specific integrated circuit (ASIC) in electrical communication with the conductive member of the capacitive pressure sensing component and the elongate flexible element;

a processing system configured to process data obtained by the pressure-sensing apparatus; and an interface configured to communicatively couple the pressure-sensing apparatus to the processing system.

* * * * *